United States Patent [19]
Hase et al.

[11] Patent Number: 5,532,257
[45] Date of Patent: Jul. 2, 1996

[54] BENZOTHIAZOLE COMPOUND, PRODUCTION THEREOF AND USE THEREOF

[75] Inventors: Takema Hase, Hamuro; Takahiro Kumonaka, Hadano; Chikako Shimizu, Shizuoka; Hiroshi Hosono, Ibaraki; Tomoji Aotsuka, Hamura; Yoshiyuki Nakamura, Shizuoka; Tetsuo Matsui, Tsukuba; Hiromichi Ishikawa, Kobe, all of Japan

[73] Assignees: Senju Pharmaceutical Co., Ltd; The Green Cross Corporation, both of Osaka, Japan

[21] Appl. No.: 343,489

[22] PCT Filed: Mar. 25, 1994

[86] PCT No.: PCT/JP94/00490

§ 371 Date: Nov. 25, 1994

§ 102(e) Date: Nov. 25, 1994

[87] PCT Pub. No.: WO94/22845

PCT Pub. Date: Oct. 13, 1994

[30] Foreign Application Priority Data

Mar. 26, 1993 [JP] Japan .................................. 5-90550

[51] Int. Cl.⁶ ...................... A61K 31/425; C07D 277/64
[52] U.S. Cl. .............................................. 514/367; 548/180
[58] Field of Search ............................. 548/180; 514/367

[56] References Cited

FOREIGN PATENT DOCUMENTS

| | | |
|---|---|---|
| 2329495 | 1/1974 | Germany . |
| 57-40478 | 3/1982 | Japan . |
| 3107970 | 5/1988 | Japan . |

OTHER PUBLICATIONS

J. Med. Chem., 15(5), 1972, 523–29.
Chem. Pharm. Bull., 21(1), 1973, 184–90.
Reddy et al., Synth. Comm., 21(2), 173–181, (1991).

Primary Examiner—Johann Richter
Assistant Examiner—Laura R. Cross
Attorney, Agent, or Firm—Sughrue, Mion, Zinn, Macpeak & Seas

[57] ABSTRACT

Production of a benzothiazole compound of the formula (I)

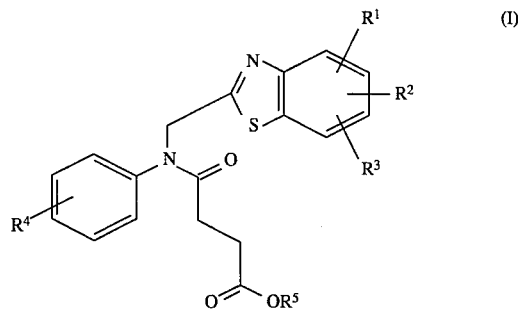

wherein $R^1$ is a halogen atom, $R^2$ and $R^3$ may be the same or different and each is a hydrogen atom or a halogen atom, $R^4$ is a hydrogen atom, a halogen atom, a lower alkyl, an alkoxy or an alkyl mercapto and $R^5$ is a hydrogen atom or a lower alkyl, or a pharmaceutically acceptable salt thereof.

The compound of the formula (I) and a pharmaceutically acceptable salt thereof of the present invention have an aldose reductase inhibitory activity in mammals inclusive of human and have superior safety. Accordingly, they are useful as pharmaceutical compositions for the treatment of the complications of diabetes, such as faulty union of corneal injury, cataract, neurosis, retinopathy and nephropathy, particularly cataract and neurosis.

12 Claims, No Drawings

BENZOTHIAZOLE COMPOUND, PRODUCTION THEREOF AND USE THEREOF

This application is a 371 of PCT/JP94/00490 filed Mar. 25, 1994.

TECHNICAL FIELD

The present invention relates to a novel benzothiazole compound having superior aldose reductase inhibitory activity and a pharmaceutically acceptable salt thereof (hereinafter generally referred to as "compound of the invention"); an intermediate for producing the compound of the invention; production thereof; and pharmaceutical compositions containing the compound of the invention.

The aforementioned compound of the invention is useful as an aldose reductase inhibitor, as well as for the prevention and/or treatment of the complications of diabetes, such as faulty union of corneal injury, diabetic cataract, retinopathy, nephropathy and neurosis.

BACKGROUND ART

Traditionally, blood sugar regulators such as insulin and synthetic hypoglycemic agents have been widely used for treating diabetes. Diabetes is a disease which accompanies various complications which are hardly prevented from developing by a mere control of the blood sugar, and a new therapeutic agent for the complications of diabetes has been demanded. Accumulation of and increase in sorbitol and galactitol in tissues which are caused by chronic hyperglycemia have recently been drawing attention as the mechanism of the onset of the complications of diabetes.

Some literatures suggest that a compound having an inhibitory action on the activity of aldose reductase, which is an enzyme capable of converting aldose such as glucose or galactose into sorbitol or galactitol, is useful for the treatment of the complications of diabetes, such as faulty union of corneal injury, cataract, retinopathy, nephropathy and neurosis [see J. H. Kinoshita et al. Biochem. Biophys. Acta, 158, 472 (1968), Richard Poulson et al, Biochem. Pharmacol., 32, 1495 (1983) and D. Dvornik et al, Science, 182, 1145 (1973)].

Based on the foregoing, the study is directed to the prevention and treatment of the complications of diabetes by the inhibition of aldose reductase activity to ultimately inhibit accumulation of polyols such as sorbitol and galactitol.

Japanese Patent Unexamined Publication Nos. 40478/1982 and 107970/1988 describe that various compounds synthesized for this end have aldose reductase inhibitory action. Yet, the development of a therapeutic agent for the complications of diabetes, which has a still more excellent aldose reductase inhibitory action, is desired.

DISCLOSURE OF THE INVENTION

In view of the above, the present inventors have conducted intensive studies with the aim of developing a therapeutic agent for the complications of diabetes, which has an aldose reductase inhibitory action, and found that benzothiazole compounds of the following formula (I)

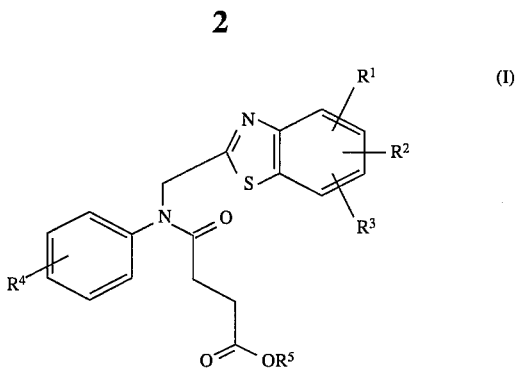

wherein $R^1$ is a halogen atom, $R^2$ and $R^3$ may be the same or different and each is a hydrogen atom or a halogen atom, $R^4$ is a hydrogen atom, a halogen atom, a lower alkyl, an alkoxy or an alkyl mercapto and $R^5$ is a hydrogen atom or a lower alkyl, and pharmaceutically acceptable salts thereof can achieve the object and established a method for the efficient production of said compounds, which resulted in the completion of the invention.

That is, the present invention provides the benzothiazole compounds of the above-mentioned formula (I) and pharmaceutically acceptable salts thereof; a method for producing benzothiazole compounds of the above formula (I) and pharmaceutically acceptable salts thereof, comprising reacting a compound of the formula (II)

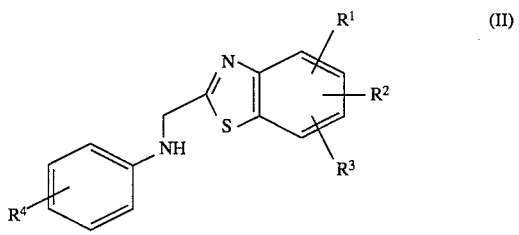

wherein $R^1$, $R^2$, $R^3$ and $R^4$ are as defined above, or a salt thereof, with a compound of the formula (III)

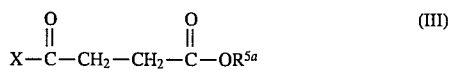

wherein X is a halogen atom and $R^{5a}$ is a lower alkyl, followed by hydrolysis on demand, or reacting a compound of the formula (IV)

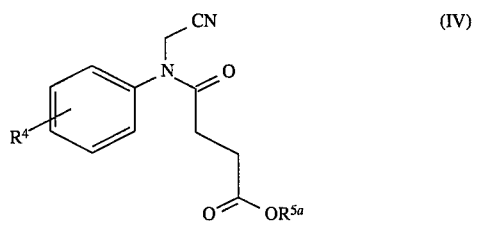

wherein $R^4$ and $R^{5a}$ are as defined above, or a salt thereof, with a compound of the formula (V)

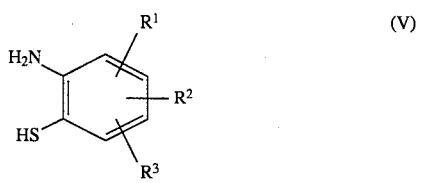

wherein $R^1$, $R^2$ and $R^3$ are as defined above, or an acid addition salt thereof, followed by hydrolysis on demand; and pharmaceutical compositions containing a benzothiazole compound of the above formula (I) or a pharmaceutically acceptable salt thereof as an active ingredient.

The present invention also provides compounds of the formula (II), salts thereof, compounds of the formula (IV) and salts thereof, which are the intermediates for producing the compounds of the prensent invention, and methods for producing them.

The halogen atom in the present invention includes, for example, fluorine atom, chlorine atom, bromine atom and iodine atom. The lower alkyl is preferably a straight or branched alkyl having 1 to 6 carbon atoms, such as methyl, ethyl, propyl, isopropyl, butyl, isobutyl, sec-butyl, tert-butyl, pentyl, isopentyl, sec-pentyl, tert-pentyl, hexyl, isohexyl, sec-hexyl and tert-hexyl. The lower alkyl may be substituted by aryl, amino, halogen atom (those mentioned above), cyano, hydroxyl etc.

The alkoxy and alkyl mercapto are preferably derived from the aforementioned lower alkyl and are exemplified by methoxy, methyl mercapto and the like.

$R^1$, $R^2$ and $R^3$ can be bonded at an optional position from 4 to 7 positions of benzothiazole. It is preferable that two of them should be bonded at the 4 and 5-positions, 5 and 7-positions, or 6 and 7-positions; more preferably, $R^1$, $R^2$ and $R^3$ are bonded at the 4, 5 and 7-positions. It is also preferable that at least one of $R^1$, $R^2$ and $R^3$, preferably all, should be fluorine atom or chlorine atom.

$R^4$ can take any optional position from 2 to 4 positions of phenyl. When $R^4$ is lower alkyl, alkoxy or alkyl mercapto having 3 or more carbon atoms, it is preferably bonded at the 3 or 4-position. In particular, 4-position is preferable when $R^4$ is a branched chain. $R^4$ is particularly preferably hydrogen atom, methyl, ethyl, propyl, isopropyl, butyl, tert-butyl, their alkoxy (e.g. methoxy) or alkyl mercapto (e.g. methyl mercapto), chlorine atom, bromine atom or fluorine atom.

$R^5$ is particularly preferably hydrogen atom, methyl or ethyl and $R^{5a}$ is particularly preferably methyl, ethyl or propyl.

The benzothiazole compound of the formula (I) may be in the form of a pharmaceutically acceptable salt. Such salt is exemplified by alkali metal salts such as lithium, sodium, potassium etc., alkaline earth metal salts such as calcium, magnesium, beryllium etc., aluminium salt, and organic salts such as triethylamine, pyridine etc.

The compounds of the formula (I) can be produced by various methods. A representative production method is described in the following.

Production 1

A compound of the formula (II)

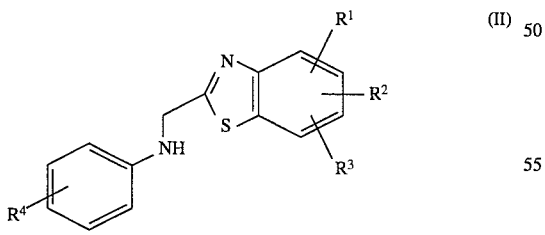

wherein $R^1$, $R^2$, $R^3$ and $R^4$ are as defined above, or a salt thereof [preferably that similar to the pharmaceutically acceptable salt of the benzothiazole compound of the formula (I)] is reacted with a compound of the formula (III)

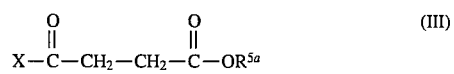

wherein X and $R^{5a}$ are as defined above, with preference given to chlorine atom or bromine atom for X, in the presence of a base where necessary, preferably under an inert gas (e.g. argon, helium, nitrogen) atmosphere, followed by hydrolysis on demand.

Examples of the base include triethylamine, N,N-diisopropylethylamine, pyridine, 1,8-diazabicyclo[5,4,0]undeca-7-ene and 4-(dimethylamino)pyridine.

The aforementioned reaction is generally carried out in various conventional solvents such as chloroform, dichloromethane, 1,2-dichloroethane, 1,2-dimethoxyethane, benzene and toluene, which do not exert adverse influence on the reaction or a mixture thereof. The specifically preferable solvents are chloroform and dichloromethane.

While the reaction temperature is not subject to any particular limitation, it is preferably $-50°$ C.$-150°$ C., particularly preferably $-20°$$-80°$ C.

The hydrolysis is carried out by conventional steps in the presence of a base. The preferable base includes, for example, alkali metal hydroxides such as sodium hydroxide and potassium hydroxide, and alkali metal carbonates such as sodium carbonate and potassium carbonate.

The reaction generally proceeds in the presence of a conventional solvent which does not exert adverse influence on the reaction, such as water, acetone, dioxane, dichloromethane, methanol, ethanol, propanol, pyridine, N,N-dimethylformamide and a mixture thereof.

The reaction temperature is not subject to any particular limitation, and the reaction proceeds at a temperature of from under cooling to under heating.

Production 2

The compound of the present invention is produced by reacting a compound of the formula (IV)

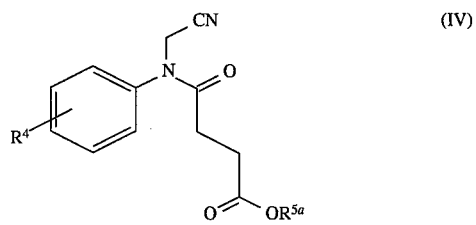

wherein $R^4$ and $R^{5a}$ are as defined above, or a salt thereof [preferably that similar to the pharmaceutically acceptable salt of the benzothiazole compound of the formula (I)] with a compound of the formula (V)

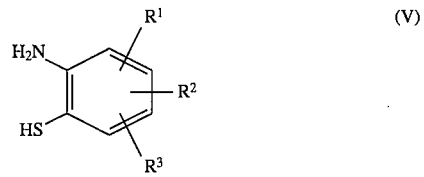

wherein $R^1$, $R^2$ and $R^3$ are as defined above, or an acid addition salt (e.g. hydrochloride) thereof in the presence of an acid if necessary, preferably under an inert gas (e.g. argon, helium, nitrogen) atmosphere, followed by hydrolysis on demand.

The instant reaction is generally carried out in a solvent which is preferably methanol, ethanol or propanol. Examples of the acid include inorganic acids such as hydrochloric acid, hydrobromic acid, sulfuric acid and nitric acid and organic acids such as formic acid, acetic acid and propionic acid, with preference given to strong acids such as sulfuric acid and hydrochloric acid. The reaction temperature is preferably from room temperature to 200° C., particularly preferably from 60° C. to refluxing temperature.

The hydrolysis may be performed under the similar reaction conditions as in Production 1 above.

The compounds of the present invention which are obtained by the aforementioned Production 1 or 2 can be isolated and purified by conventional methods including extraction, precipitation, fractionation chromatography, partition, crystallization and recrystallization. The compounds of the present invention thus obtained can be converted to desired pharmaceutically acceptable salts by conventional methods.

The typical benzothiazole compounds of the formula (I) of the present invention are exemplified by the following.

ethyl N-[(4,5,7-trifluorobenzothiazol-2-yl)methyl]-N-(2-methylphenyl)succinamate
N-[(4,5,7-trifluorobenzothiazol-2-yl)methyl]-N-(2-methylphenyl)succinamic acid
ethyl N-[(4,5-difluorobenzothiazol-2-yl)methyl]-N-(2-methylphenyl)succinamate
N-[(4,5-difluorobenzothiazol-2-yl)methyl]-N-(2-methylphenyl)succinamic acid
ethyl N-[(5,7-difluorobenzothiazol-2-yl)methyl]-N-(2-methylphenyl)succinamate
N-[(5,7-difluorobenzothiazol-2-yl)methyl]-N-(2-methylphenyl)succinamic acid
ethyl N-[(6,7-difluorobenzothiazol-2-yl)methyl]-N-(2-methylphenyl)succinamate
N-[(6,7-difluorobenzothiazol-2-yl)methyl]-N-(2-methylphenyl)succinamic acid
ethyl N-[(4,5-dichlorobenzothiazol-2-yl)methyl]-N-(2-methylphenyl)succinamate
N-[(4,5-dichlorobenzothiazol-2-yl)methyl]-N-(2-methylphenyl)succinamic acid
ethyl N-[(4,5,7-trifluorobenzothiazol-2-yl)methyl]-N-(3-methylphenyl)succinamate
N-[(4,5,7-trifluorobenzothiazol-2-yl)methyl]-N-(3-methylphenyl)succinamic acid
ethyl N-[(4,5-difluorobenzothiazol-2-yl)methyl]-N-(3-methylphenyl)succinamate
N-[(4,5-difluorobenzothiazol-2-yl)methyl]-N-(3-methylphenyl)succinamic acid
ethyl N-[(5,7-difluorobenzothiazol-2-yl)methyl]-N-(3-methylphenyl)succinamate
N-[(5,7-difluorobenzothiazol-2-yl)methyl]-N-(3-methylphenyl)succinamic acid
ethyl N-[(6,7-difluorobenzothiazol-2-yl)methyl]-N-(3-methylphenyl)succinamate
N-[(6,7-difluorobenzothiazol-2-yl)methyl]-N-(3-methylphenyl)succinamic acid
ethyl N-[(4,5-dichlorobenzothiazol-2-yl)methyl]-N-(3-methylphenyl)succinamate
N-[(4,5-dichlorobenzothiazol-2-yl)methyl]-N-(3-methylphenyl)succinamic acid
ethyl N-[(4,5,7-trifluorobenzothiazol-2-yl)methyl]-N-(4-methylphenyl)succinamate
N-[(4,5,7-trifluorobenzothiazol-2-yl)methyl]-N-(4-methylphenyl)succinamic acid
ethyl N-[(4,5-difluorobenzothiazol-2-yl)methyl]-N-(4-methylphenyl)succinamate
N-[(4,5-difluorobenzothiazol-2-yl)methyl]-N-(4-methylphenyl)succinamic acid
ethyl N-[(5,7-difluorobenzothiazol-2-yl)methyl]-N-(4-methylphenyl)succinamate
N-[(5,7-difluorobenzothiazol-2-yl)methyl]-N-(4-methylphenyl)succinamic acid
ethyl N-[(6,7-difluorobenzothiazol-2-yl)methyl]-N-(4-methylphenyl)succinamate
N-[(6,7-difluorobenzothiazol-2-yl)methyl]-N-(4-methylphenyl)succinamic acid
ethyl N-[(4,5-dichlorobenzothiazol-2-yl)methyl]-N-(4-methylphenyl)succinamate
N-[(4,5-dichlorobenzothiazol-2-yl)methyl]-N-(4-methylphenyl)succinamic acid
ethyl N-(3-ethylphenyl)-N-[(4,5,7-trifluorobenzothiazol-2-yl)methyl]succinamate
N-(3-ethylphenyl)-N-[(4,5,7-trifluorobenzothiazol-2-yl)methyl]succinamic acid
ethyl N-(3-ethylphenyl)-N-[(4,5-difluorobenzothiazol-2-yl)methyl]succinamate
N-(3-ethylphenyl)-N-[(4,5-difluorobenzothiazol-2-yl)methyl]succinamic acid
ethyl N-(3-ethylphenyl)-N-[(5,7-difluorobenzothiazol-2-yl)methyl]succinamate
N-(3-ethylphenyl)-N-[(5,7-difluorobenzothiazol-2-yl)methyl]succinamic acid
ethyl N-(3-ethylphenyl)-N-[(6,7-difluorobenzothiazol-2-yl)methyl]succinamate
N-(3-ethylphenyl)-N-[(6,7-difluorobenzothiazol-2-yl)methyl]succinamic acid
ethyl N-[(4,5-dichlorobenzothiazol-2-yl)methyl]-N-(3-ethylphenyl)succinamate
N-[(4,5-dichlorobenzothiazol-2-yl)methyl]-N-(3-ethylphenyl)succinamic acid
ethyl N-(4-propylphenyl)-N-[(4,5,7-trifluorobenzothiazol-2-yl)methyl]succinamate
N-(4-propylphenyl)-N-[(4,5,7-trifluorobenzothiazol-2-yl)methyl]succinamic acid
ethyl N-(4-propylphenyl)-N-[(4,5-difluorobenzothiazol-2-yl)methyl]succinamate
N-(4-propylphenyl)-N-[(4,5-difluorobenzothiazol-2-yl)methyl]succinamic acid
ethyl N-(4-propylphenyl)-N-[(5,7-difluorobenzothiazol-2-yl)methyl]succinamate
N-(4-propylphenyl)-N-[(5,7-difluorobenzothiazol-2-yl)methyl]succinamic acid
ethyl N-(4-propylphenyl)-N-[(6,7-difluorobenzothiazol-2-yl)methyl]succinamate
N-(4-propylphenyl)-N-[(6,7-difluorobenzothiazol-2-yl)methyl]succinamic acid
ethyl N-(4-propylphenyl)-N-[(4,5-dichlorobenzothiazol-2-yl)methyl]succinamate
N-(4-propylphenyl)-N-[(4,5-dichlorobenzothiazol-2-yl)methyl]succinamic acid
ethyl N-[(4,5,7-trifluorobenzothiazol-2-yl)methyl]-N-(4-isopropylphenyl)succinamate
N-[(4,5,7-trifluorobenzothiazol-2-yl)methyl]-N-(4-isopropylphenyl)succinamic acid
ethyl N-[(4,5-difluorobenzothiazol-2-yl)methyl]-N-(4-isopropylphenyl)succinamate
N-[(4,5-difluorobenzothiazol-2-yl)methyl]-N-(4-isopropylphenyl)succinamic acid
ethyl N-[(5,7-difluorobenzothiazol-2-yl)methyl]-N-(4-isopropylphenyl)succinamate
N-[(5,7-difluorobenzothiazol-2-yl)methyl]-N-(4-isopropylphenyl)succinamic acid
ethyl N-[(6,7-difluorobenzothiazol-2-yl)methyl]-N-(4-isopropylphenyl)succinamate
N-[(6,7-difluorobenzothiazol-2-yl)methyl]-N-(4-isopropylphenyl)succinamic acid
ethyl N-[(4,5-dichlorobenzothiazol-2-yl)methyl]-N-(4-isopropylphenyl)succinamate
N-[(4,5-dichlorobenzothiazol-2-yl)methyl]-N-(4-isopropylphenyl)succinamic acid
ethyl N-[(4,5,7-trifluorobenzothiazol-2-yl)methyl]-N-(2-methoxyphenyl)succinamate
N-[(4,5,7-trifluorobenzothiazol-2-yl)methyl]-N-(2-methoxyphenyl)succinamic acid
ethyl N-[(4,5-difluorobenzothiazol-2-yl)methyl]-N-(2-methoxyphenyl)succinamate N-[(4,5-difluorobenzothiazol-2-yl)methyl]-N-(2-methoxyphenyl)succinamic acid
ethyl N-[(5,7-difluorobenzothiazol-2-yl)methyl]-N-(2-methoxyphenyl)succinamate
N-[(5,7-difluorobenzothiazol-2-yl)methyl]-N-(2-methoxyphenyl)succinamic acid
ethyl N-[(6,7-difluorobenzothiazol-2-yl)methyl]-N-(2-methoxyphenyl)succinamate
N-[(6,7-difluorobenzothiazol-2-yl)methyl]-N-(2-methoxyphenyl)succinamic acid
ethyl N-[(4,5-dichlorobenzothiazol-2-yl)methyl]-N-(2-methoxyphenyl)succinamate
N-[(4,5-dichlorobenzothiazol-2-yl)methyl]-N-(2-methoxyphenyl)succinamic acid
ethyl N-[(4,5,7-trifluorobenzothiazol-2-yl)methyl]-N-(3-methoxyphenyl)succinamate
N-[(4,5,7-trifluorobenzothiazol-2-yl)methyl]-N-(3-methoxyphenyl)succinamic acid
ethyl N-[(4,5-difluorobenzothiazol-2-yl)methyl]-N-(3-methoxyphenyl)succinamate
N-[(4,5-difluorobenzothiazol-2-yl)methyl]-N-(3-methoxyohenyl)succinamic acid
ethyl N-[(5,7-difluorobenzothiazol-2-yl)methyl]-N-(3-methoxyphenyl)succinamate
N-[(5,7-difluorobenzothiazol-2-yl)methyl]-N-(3-methoxyphenyl)succinamic acid
ethyl N-[(6,7-difluorobenzothiazol-2-yl)methyl]-N-(3-methoxyphenyl)succinamate
N-[(6,7-difluorobenzothiazol-2-yl)methyl]-N-(3-methoxyphenyl)succinamic acid
ethyl N-[(4,5-dichlorobenzothiazol-2-yl)methyl]-N-(3-methoxyphenyl)succinamic
N-[(4,5-dichlorobenzothiazol-2-yl)methyl]-N-(3-methoxyphenyl)succinamic acid
ethyl N-[(4,5,7-trifluorobenzothiazol-2-yl)methyl]-N-(4-methoxyphenyl)succinamate
N-[(4,5,7-trifluorobenzothiazol-2-yl)methyl]-N-(4-methoxyphenyl)succinamic acid
ethyl N-[(4,5-difluorobenzothiazol-2-yl)methyl]-N-(4-methoxyphenyl)succinamate
N-[(4,5-difluorobenzothiazol-2-yl)methyl]-N-(4-methoxyphenyl)succinamic acid
ethyl N-[(5,7-difluorobenzothiazol-2-yl)methyl]-N-(4-methoxyphenyl)succinamate
N-[(5,7-difluorobenzothiazol-2-yl)methyl]-N-(4-methoxyphenyl)succinamic acid
ethyl N-[(6,7-difluorobenzothiazol-2-yl)methyl]-N-(4-methoxyphenyl)succinamate
N-[(6,7-difluorobenzothiazol-2-yl)methyl]-N-(4-methoxyphenyl)succinamic acid
ethyl N-[(4,5-dichlorobenzothiazol-2-yl)methyl]-N-(4-methoxyphenyl)succinamate
N-[(4,5-dichlorobenzothiazol-2-yl)methyl]-N-(4-methoxyphenyl)succinamic acid
ethyl N-(3-ethoxyphenyl)-N-[(4,5,7-trifluorobenzothiazol-2-yl)methyl]succinamate
N-(3-ethoxyphenyl)-N-[(4,5,7-trifluorobenzothiazol-2-yl)methyl]succinamic acid
ethyl N-(3-ethoxyphenyl)-N-[(4,5-difluorobenzothiazol-2-yl)methyl]succinamate
N-(3-ethoxyphenyl)-N-[(4,5-difluorobenzothiazol-2-yl)methyl]succinamic acid
ethyl N-(3-ethoxyphenyl)-N-[(5,7-difluorobenzothiazol-2-yl)methyl]succinamate
N-(3-ethoxyphenyl)-N-[(5,7-difluorobenzothiazol-2-yl)methyl]succinamic acid
ethyl N-(3-ethoxyphenyl)-N-[(6,7-difluorobenzothiazol-2-yl)methyl]succinamate
N-(3-ethoxyphenyl)-N-[(6,7-difluorobenzothiazol-2-yl)methyl]succinamic acid
ethyl N-[(4,5-dichlorobenzothiazol-2-yl)methyl]-N-(3-ethoxyphenyl)succinamate
N-[(4,5-dichlorobenzothiazol-2-yl)methyl]-N-(3-ethoxyphenyl)succinamic acid
ethyl N-[(4,5,7-trifluorobenzothiazol-2-yl)methyl]-N-(4propoxyphenyl)succinamate
N-[(4,5,7-trifluorobenzothiazol-2-yl)methyl]-N-(4-propoxyphenyl)succinamic acid
ethyl N-[(4,5-difluorobenzothiazol-2-yl)methyl]-N-(4-propoxyphenyl)succinamate
N-[(4,5-difluorobenzothiazol-2-yl)methyl]-N-(4-propoxyphenyl)succinamic acid
ethyl N-[(5,7-difluorobenzothiazol-2-yl)methyl]-N-(4-propoxyphenyl)succinamate
N-[(5,7-difluorobenzothiazol-2-yl)methyl]-N-(4-propoxyphenyl)succinamic acid
ethyl N-[(6,7-difluorobenzothiazol-2-yl)methyl]-N-(4-propoxyphenyl)succinamate
N-[(6,7-difluorobenzothiazol-2-yl)methyl]-N-(4-propoxyphenyl)succinamic acid
ethyl N-[(4,5-dichlorobenzothiazol-2-yl)methyl]-N-(4-propoxyphenyl)succinamate
N-[(4,5-dichlorobenzothiazol-2-yl)methyl]-N-(4-propoxyphenyl)succinamic acid
ethyl N-[(4,5,7-trifluorobenzothiazol-2-yl)methyl]-N-(2-methylthiophenyl)succinamate
N-[(4,5,7-trifluorobenzothiazol-2-yl)methyl]-N-(2-methylthiophenyl)succinamic acid
ethyl N-[(4,5-difluorobenzothiazol-2-yl)methyl]-N-(2-methylthiophenyl)succinamate
N-[(4,5-difluorobenzothiazol-2-yl)methyl]-N-(2-methylthiophenyl)succinamic acid
ethyl N-[(5,7-difluorobenzothiazol-2-yl)methyl]-N-(2-methylthiophenyl)succinamate
N-[(5,7-difluorobenzothiazol-2-yl)methyl]-N-(2-methylthiophenyl)succinamic acid
ethyl N-[(6,7-difluorobenzothiazol-2-yl)methyl]-N-(2-methylthiophenyl)succinamate
N-[(6,7-difluorobenzothiazol-2-yl)methyl]-N-(2-methylthiophenyl)succinamic acid
ethyl N-[(4,5-dichlorobenzothiazol-2-yl)methyl]-N-(2-methylthiophenyl)succinamate
N-[(4,5-dichlorobenzothiazol-2-yl)methyl]-N-(2-methylthiophenyl)succinamic acid
ethyl N-[(4,5,7-trifluorobenzothiazol-2-yl)methyl]-N-(3-methylthiophenyl)succinamate
N-[(4,5,7-trifluorobenzothiazol-2-yl)methyl]-N-(3-methylthiophenyl)succinamic acid
ethyl N-[(4,5-difluorobenzothiazol-2-yl)methyl]-N-(3-methylthiophenyl)succinamate
N-[(4,5-difluorobenzothiazol-2-yl)methyl]-N-(3-methylthiophenyl)succinamic acid
ethyl N-[(5,7-difluorobenzothiazol-2-yl)methyl]-N-(3-methylthiophenyl)succinamate
N-[(5,7-difluorobenzothiazol-2-yl)methyl]-N-(3-methylthiophenyl)succinamic acid
ethyl N-[(6,7-difluorobenzothiazol-2-yl)methyl]-N-(3-methylthiophenyl)succinamate
N-[(6,7-difluorobenzothiazol-2-yl)methyl]-N-(3-methylthiophenyl)succinamic acid
ethyl N-[(4,5-dichlorobenzothiazol-2-yl)methyl]-N-(3-methylthiophenyl)succinamate
N-[(4,5-dichlorobenzothiazol-2-yl)methyl]-N-(3-methylthiophenyl)succinamic acid
ethyl N-[(4,5,7-trifluorobenzothiazol-2-yl)methyl]-N-(4-methylthiophenyl)succinamate N-[(4,5,7-trifluorobenzothiazol-2-yl)methyl]-N-(4-methylthiophenyl)succinamic acid
ethyl N-[(4,5-difluorobenzothiazol-2-yl)methyl]-N-(4-methylthiophenyl)succinamate
N-[(4,5-difluorobenzothiazol-2-yl)methyl]-N-(4-methylthiophenyl)succinamic acid
ethyl N-[(5,7-difluorobenzothiazol-2-yl)methyl]-N-(4-methylthiophenyl)succinamate
N-[(5,7-difluorobenzothiazol-2-yl)methyl]-N-(4-methylthiophenyl)succinamic acid
ethyl N-[(6,7-difluorobenzothiazol-2-yl)methyl]-N-(4-methylthiophenyl)succinamate
N-[(6,7-difluorobenzothiazol-2-yl)methyl]-N-(4-methylthiophenyl)succinamic acid
ethyl N-[(4,5-dichlorobenzothiazol-2-yl)methyl]-N-(4-methylthiophenyl)succinamate
N-[(4,5-dichlorobenzothiazol-2-yl)methyl]-N-(4-methylthiophenyl)succinamic acid
ethyl N-(3-ethylthiophenyl)-N-[(4,5,7-trifluorobenzothiazol-2yl)methyl]succinamate
N-(3-ethylthiophenyl)-N-[(4,5,7-trifluorobenzothiazol-2-yl)methyl]succinamic acid
ethyl N-(3-ethylthiophenyl)-N-[(4,5-difluorobenzothiazol-2yl)methyl]succinamate
N-(3-ethylthiophenyl)-N-[(4,5-difluorobenzothiazol-2-yl)methyl]succinamic acid
ethyl N-(3-ethylthiophenyl)-N-[(5,7-difluorobenzothiazol-2yl)methyl]succinamate
N-(3-ethylthiophenyl)-N-[(5,7-difluorobenzothiazol-2-yl)methyl]succinamic acid
ethyl N-(3-ethylthiophenyl)-N-[(6,7-difluorobenzothiazol-2yl)methyl]succinamate
N-(3-ethylthiophenyl)-N-[(6,7-difluorobenzothiazol-2-yl)methyl]succinamic acid
ethyl N-[(4,5-dichlorobenzothiazol-2-yl)methyl]-N-(3-ethylthiophenyl)succinamate
N-[(4,5-dichlorobenzothiazol-2-yl)methyl]-N-(3-ethylthiophenyl)succinamic acid
ethyl N-[(4,5,7-trifluorobenzothiazol-2-yl)methyl]-N-(4-propylthiophenyl)succinamate
N-[(4,5,7-trifluorobenzothiazol-2-yl)methyl]-N-(4-propylthiophenyl)succinamic acid
ethyl N-[(4,5-difluorobenzothiazol-2-yl)methyl]-N-(4-propylthiophenyl)succinamate
N-[(4,5-difluorobenzothiazol-2-yl)methyl]-N-(4-propylthiophenyl)succinamic acid
ethyl N-[(5,7-difluorobenzothiazol-2-yl)methyl]-N-(4-propylthiophenyl)succinamate
N-[(5,7-difluorobenzothiazol-2-yl)methyl]-N-(4-propylthiophenyl)succinamic acid
ethyl N-[(6,7-difluorobenzothiazol-2-yl)methyl]-N-(4-propylthiophenyl)succinamate
N-[(6,7-difluorobenzothiazol-2-yl)methyl]-N-(4-propylthiophenyl)succinamic acid
ethyl N-[(4,5-dichlorobenzothiazol-2-yl)methyl]-N-(4-propylthiophenyl)succinamate
N-[(4,5-dichlorobenzothiazol-2-yl)methyl]-N-(4-propylthiophenyl)succinamic acid
ethyl N-(2-chlorophenyl)-N-[(4,5,7-trifluorobenzothiazol-2-yl)methyl]succinamate
N-(2-chlorophenyl)-N-[(4,5,7-trifluorobenzothiazol-2-yl)methyl]succinamic acid
ethyl N-(2-chlorophenyl)-N-[(4,5-difluorobenzothiazol-2-yl)methyl]succinamate
N-(2-chlorophenyl)-N-[(4,5-difluorobenzothiazol-2-yl)methyl]succinamic acid
ethyl N-(2-chlorophenyl)-N-[(5,7-difluorobenzothiazol-2-yl)methyl]succinamate
N-(2-chlorophenyl)-N-[(5,7-difluorobenzothiazol-2-yl)methyl]succinamic acid
ethyl N-(2-chlorophenyl)-N-[(6,7-difluorobenzothiazol-2-yl)methyl]succinamate
N-(2-chlorophenyl)-N-[(6,7-difluorobenzothiazol-2-yl)methyl]succinamic acid
ethyl N-(2-chlorophenyl)-N-[(4,5-dichlorobenzothiazol-2-yl)methyl]succinamate
N-(2-chlorophenyl)-N-[(4,5-dichlorobenzothiazol-2-yl)methyl]succinamic acid
ethyl N-(3-chlorophenyl)-N-[(4,5,7-trifluorobenzothiazol-2-yl)methyl]succinamate
N-(3-chlorophenyl)-N-[(4,5,7-trifluorobenzothiazol-2-yl)methyl]succinamic acid
ethyl N-(3-chlorophenyl)-N-[(4,5-difluorobenzothiazol-2-yl)methyl]succinamate
N-(3-chlorophenyl)-N-[(4,5-difluorobenzothiazol-2-yl)methyl]succinamic acid
ethyl N-(3-chlorophenyl)-N-[(5,7-difluorobenzothiazol-2-yl)methyl]succinamate
N-(3-chlorophenyl)-N-[(5,7-difluorobenzothiazol-2-yl)methyl]succinamic acid
ethyl N-(3-chlorophenyl)-N-[(6,7-difluorobenzothiazol-2-yl)methyl]succinamate
N-(3-chlorophenyl)-N-[(6,7-difluorobenzothiazol-2-yl)methyl]succinamic acid
ethyl N-(3-chlorophenyl)-N-[(4,5-dichlorobenzothiazol-2-yl)methyl]succinamate
N-(3-chlorophenyl)-N-[(4,5-dichlorobenzothiazol-2-yl)methyl]succinamic acid
ethyl N-(4-chlorophenyl)-N-[(4,5,7-trifluorobenzothiazol-2-yl)methyl]succinamate
N-(4-chlorophenyl)-N-[(4,5,7-trifluorobenzothiazol-2-yl)methyl]succinamic acid
ethyl N-(4-chlorophenyl)-N-[(4,5-difluorobenzothiazol-2-yl)methyl]succinamate
N-(4-chlorophenyl)-N-[(4,5-difluorobenzothiazol-2-yl)methyl]succinamic acid
ethyl N-(4-chlorophenyl)-N-[(5,7-difluorobenzothiazol-2-yl)methyl]succinamate
N-(4-chlorophenyl)-N-[(5,7-difluorobenzothiazol-2-yl)methyl]succinamic acid
ethyl N-(4-chlorophenyl)-N-[(6,7-difluorobenzothiazol-2-yl)methyl]succinamate
N-(4-chlorophenyl)-N-[(6,7-difluorobenzothiazol-2-yl)methyl]succinamic acid
ethyl N-(4-chlorophenyl)-N-[(4,5-dichlorobenzothiazol-2-yl)methyl]succinamate
N-(4-chlorophenyl)-N-[(4,5-dichlorobenzothiazol-2-yl)methyl]succinamic acid
ethyl N-(2-bromophenyl)-N-[(4,5,7-trifluorobenzothiazol-2-yl)methyl]succinamate
N-(2-bromophenyl)-N-[(4,5,7-trifluorobenzothiazol-2-yl)methyl]succinamic acid
ethyl N-(2-bromophenyl)-N-[(4,5-difluorobenzothiazol-2-yl)methyl]succinamate
N-(2-bromophenyl)-N-[(4,5-difluorobenzothiazol-2-yl)methyl]succinamic acid
ethyl N-(2-bromophenyl)-N-[(5,7-difluorobenzothiazol-2-yl)methyl]succinamate
N-(2-bromophenyl)-N-[(5,7-difluorobenzothiazol-2-yl)methyl]succinamic acid
ethyl N-(2-bromophenyl)-N-[(6,7-difluorobenzothiazol-2-yl)methyl]succinamate
N-(2-bromophenyl)-N-[(6,7-difluorobenzothiazol-2-yl)methyl]succinamic acid
ethyl N-(2-bromophenyl)-N-[(4,5-dichlorobenzothiazol-2-yl)methyl]succinamate N-(2-bromophenyl)-N-[(4,5-dichlorobenzothiazol-2-yl)methyl]succinamic acid
ethyl N-(3-bromophenyl)-N-[(4,5,7-trifluorobenzothiazol-2-yl)methyl]succinamate
N-(3-bromophenyl)-N-[(4,5,7-trifluorobenzothiazol-2-yl)methyl]succinamic acid
ethyl N-(3-bromophenyl)-N-[(4,5-difluorobenzothiazol-2-yl)-methyl]succinamate
N-(3-bromophenyl)-N-[(4,5-difluorobenzothiazol-2-yl)methyl]succinamic acid
ethyl N-(3-bromophenyl)-N-[(5,7-difluorobenzothiazol-2-yl)methyl]succinamate
N-(3-bromophenyl)-N-[(5,7-difluorobenzothiazol-2-yl)methyl]succinamic acid
ethyl N-(3-bromophenyl)-N-[(6,7-difluorobenzothiazol-2-yl)methyl]succinamate
N-(3-bromophenyl)-N-[(6,7-difluorobenzothiazol-2-yl)methyl]succinamic acid
ethyl N-(3-bromophenyl)-N-[(4,5-dichlorobenzothiazol-2-yl)methyl]succinamate
N-(3-bromophenyl)-N-[(4,5-dichlorobenzothiazol-2-yl)methyl]succinamic acid
ethyl N-(4-bromophenyl)-N-[(4,5,7-trifluorobenzothiazol-2-yl)methyl]succinamate
N-(4-bromophenyl)-N-[(4,5,7-trifluorobenzothiazol-2-yl)methyl]succinamic acid
ethyl N-(4-bromophenyl)-N-[(4,5-difluorobenzothiazol-2-yl)methyl]succinamate
N-(4-bromophenyl)-N-[(4,5-difluorobenzothiazol-2-yl)methyl]succinamic acid
ethyl N-(4-bromophenyl)-N-[(5,7-difluorobenzothiazol-2-yl)methyl]succinamate
N-(4-bromophenyl)-N-[(5,7-difluorobenzothiazol-2-yl)methyl]succinamic acid
ethyl N-(4-bromophenyl)-N-[(6,7-difluorobenzothiazol-2-yl)methyl]succinamate
N-(4-bromophenyl)-N-[(6,7-difluorobenzothiazol-2-yl)methyl]succinamic acid
ethyl N-(4-bromophenyl)-N-[(4,5-dichlorobenzothiazol-2-yl)methyl]succinamate
N-(4-bromophenyl)-N-[(4,5-dichlorobenzothiazol-2-yl)methyl]succinamic acid
ethyl N-(2-fluorophenyl)-N-[(4,5,7-trifluorobenzothiazol-2yl)methyl]succinamate
N-(2-fluorophenyl)-N-[(4,5,7-trifluorobenzothiazol-2-yl)methyl]succinamic acid
ethyl N-(2-fluorophenyl)-N-[(4,5-difluorobenzothiazol-2-yl)methyl]succinamate
N-(2-fluorophenyl)-N-[(4,5-difluorobenzothiazol-2-yl)methyl]succinamic acid
ethyl N-(2-fluorophenyl)-N-[(5,7-difluorobenzothiazol-2-yl)methyl]succinamate
N-(2-fluorophenyl)-N-[(5,7-difluorobenzothiazol-2-yl)methyl]succinamic acid
ethyl N-(2-fluorophenyl)-N-[(6,7-difluorobenzothiazol-2-yl)methyl]succinamate
N-(2-fluorophenyl)-N-[(6,7-difluorobenzothiazol-2-yl)methyl]-succinamic acid
ethyl N-(2-fluorophenyl)-N-[(4,5-dichlorobenzothiazol-2-yl)methyl]succinamate
N-(2-fluorophenyl)-N-[(4,5-dichlorobenzothiazol-2-yl)methyl]succinamic acid
ethyl N-(3-fluorophenyl)-N-[(4,5,7-trifluorobenzothiazol-2-yl)methyl]succinamate
N-(3-fluorophenyl)-N-[(4,5,7-trifluorobenzothiazol-2-yl)methyl]succinamic acid
ethyl N-(3-fluorophenyl)-N-[(4,5-difluorobenzothiazol-2-yl)methyl]succinamate
N-(3-fluorophenyl)-N-[(4,5-difluorobenzothiazol-2-yl)methyl]succinamic acid
ethyl N-(3-fluorophenyl)-N-[(5,7-difluorobenzothiazol-2-yl)methyl]succinamate
N-(3-fluorophenyl)-N-[(5,7-difluorobenzothiazol-2-yl)methyl]succinamic acid
ethyl N-(3-fluorophenyl)-N-[(6,7-difluorobenzothiazol-2-yl)methyl]succinamate
N-(3-fluorophenyl)-N-[(6,7-difluorobenzothiazol-2-yl)methyl]succinamic acid
ethyl N-(3-fluorophenyl)-N-[(4,5-dichlorobenzothiazol-2-yl)methyl]succinamate
N-(3-fluorophenyl)-N-[(4,5-dichlorobenzothiazol-2-yl)methyl]succinamic acid
ethyl N-(4-fluorophenyl)-N-[(4,5,7-trifluorobenzothiazol-2yl)methyl]succinamate
N-(4-fluorophenyl)-N-[(4,5,7-trifluorobenzothiazol-2-yl)methyl]succinamic acid
ethyl N-(4-fluorophenyl)-N-[(4,5-difluorobenzothiazol-2-yl)methyl]succinamate
N-(4-fluorophenyl)-N-[(4,5-difluorobenzothiazol-2-yl)methyl]succinamic acid
ethyl N-(4-fluorophenyl)-N-[(5,7-difluorobenzothiazol-2-yl)methyl]succinamate
N-(4-fluorophenyl)-N-[(5,7-difluorobenzothiazol-2-yl)methyl]succinamic acid
ethyl N-(4-fluorophenyl)-N-[(6,7-difluorobenzothiazol-2-yl)methyl]succinamate
N-(4-fluorophenyl)-N-[(6,7-difluorobenzothiazol-2-yl)methyl]succinamic acid
ethyl N-(4-fluorophenyl)-N-[(4,5-dichlorobenzothiazol-2-yl)methyl]succinamate
N-(4-fluorophenyl)-N-[(4,5-dichlorobenzothiazol-2-yl)methyl]succinamic acid
ethyl N-[(4,5,7-trifluorobenzothiazol-2-yl)methyl]-N-phenylsuccinamate
N-[(4,5,7-trifluorobenzothiazol-2-yl)methyl]-N-phenylsuccinamic acid
ethyl N-[(4,5-difluorobenzothiazol-2-yl)methyl]-N-phenylsuccinamate
N-[(4,5-difluorobenzothiazol-2-yl)methyl]-N-phenylsuccinamic acid
ethyl N-[(5,7-difluorobenzothiazol-2-yl)methyl]-N-phenylsuccinamate
N-[(5,7-difluorobenzothiazol-2-yl)methyl]-N-phenylsuccinamic acid
ethyl N-[(6,7-difluorobenzothiazol-2-yl)methyl]-N-phenylsuccinamate
N-[(6,7-difluorobenzothiazol-2-yl)methyl]-N-phenylsuccinamic acid
ethyl N-[(4,5-dichlorobenzothiazol-2-yl)methyl]-N-phenylsuccinamate
N-[(4,5-dichlorobenzothiazol-2-yl)methyl]-N-phenylsuccinamic acid The compound of the formula (II) and a salt thereof used as intermediates in the aforementioned Production 1 are novel compounds and can be produced by the following method.

That is, a compound of the formula (V)

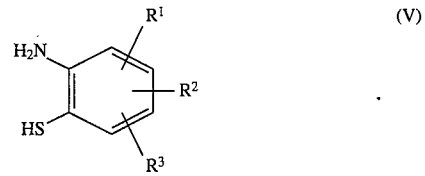

wherein $R^1$, $R^2$ and $R^3$ are as defined above or an acid addition salt thereof is reacted with a compound of the formula (VI)

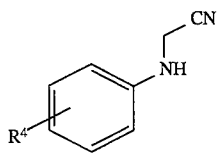 (VI)

wherein $R^4$ is as defined above, or a salt thereof [preferably that similar to the pharmaceutically acceptable salt of the benzothiazole compound of the formula (I)] under the reaction conditions similar to those in the aforementioned Production 2.

The starting compound of the formula (V) inclusive of salt thereof are known or can be easily produced by a known method [Journal of Medicinal Chemistry, 34, 108–122 (1991)]. The starting compound of the formula (VI) inclusive of salt thereof are known or can be easily produced by a known method [*Hev. Chim. Acta*, 37, 166–178 (1954)].

The typical compounds of the formula (II) which are intermediates of the present invention are exemplified by the following compounds.

N-(2-methylphenyl)[(4,5,7-trifluorobenzothiazol-2-yl)methyl]amine
N-(2-methylphenyl)[(4,5-difluorobenzothiazol-2-yl)methyl]amine
N-(2-methylphenyl)[(5,7-difluorobenzothiazol-2-yl)methyl]amine
N-(2-methylphenyl)[(6,7-difluorobenzothiazol-2-yl)methyl]amine
N-(2-methylphenyl)[(4,5-dichlorobenzothiazol-2-yl)methyl]amine
N-(4-methylphenyl)[(4,5,7-trifluorobenzothiazol-2-yl)methyl]amine
N-(4-methylphenyl)[(4,5-difluorobenzothiazol-2-yl)methyl]amine
N-(4-methylphenyl)[(5,7-difluorobenzothiazol-2-yl)methyl]amine
N-(4-methylphenyl)[(6,7-difluorobenzothiazol-2-yl)methyl]amine
N-(4-methylphenyl)[(4,5-dichlorobenzothiazol-2-yl)methyl]amine
N-(3-propylphenyl)[(4,5,7-trifluorobenzothiazol-2-yl)methyl]amine
N-(3-propylphenyl)[(4,5-difluorobenzothiazol-2-yl)methyl]amine
N-(3-propylphenyl)[(5,7-difluorobenzothiazol-2-yl)methyl]amine
N-(3-propylphenyl)[(6,7-difluorobenzothiazol-2-yl)methyl]amine
N-(3-propylphenyl)[(4,5-dichlorobenzothiazol-2-yl)methyl]amine
N-(4-isopropylphenyl)[(4,5,7-trifluorobenzothiazol-2-yl)methyl]amine
N-(4-isopropylphenyl)[(4,5-difluorobenzothiazol-2-yl)methyl]amine
N-(4-isopropylphenyl)[(5,7-difluorobenzothiazol-2-yl)methyl]amine
N-(4-isopropylphenyl)[(6,7-difluorobenzothiazol-2-yl)methyl]amine
N-(4-isopropylphenyl)[(4,5-dichlorobenzothiazol-2-yl)methyl]amine
N-(2-methoxyphenyl)[(4,5,7-trifluorobenzothiazol-2-yl)methyl]amine
N-(2-methoxyphenyl)[(4,5-difluorobenzothiazol-2-yl)methyl]amine
N-(2-methoxyphenyl)[(5,7-difluorobenzothiazol-2-yl)methyl]amine
N-(2-methoxyphenyl)[(6,7-difluorobenzothiazol-2-yl)methyl]amine
N-(2-methoxyphenyl)[(4,5-dichlorobenzothiazol-2-yl)methyl]amine
N-(3-ethoxyphenyl)[(4,5,7-trifluorobenzothiazol-2-yl)methyl]amine
N-(3-ethoxyphenyl)[(4,5-difluorobenzothiazol-2-yl)methyl]amine
N-(3-ethoxyphenyl)[(5,7-difluorobenzothiazol-2-yl)methyl]amine
N-(3-ethoxyphenyl)[(6,7-difluorobenzothiazol-2-yl)methyl]amine
N-(3-ethoxyphenyl)[(4,5-dichlorobenzothiazol-2-yl)methyl]amine
N-(4-propoxyphenyl)[(4,5,7-trifluorobenzothiazol-2-yl)methyl]amine
N-(4-propoxyphenyl)[(4,5-difluorobenzothiazol-2-yl)methyl]amine
N-(4-propoxyphenyl)[(5,7-difluorobenzothiazol-2-yl)methyl]amine
N-(4-propoxyphenyl)[(6,7-difluorobenzothiazol-2-yl)methyl]amine
N-(4-propoxyphenyl)[(4,5-dichlorobenzothiazol-2-yl)methyl]amine
N-(2-methylthiophenyl)[(4,5,7-trifluorobenzothiazol-2-yl)methyl]amine
N-(2-methylthiophenyl)[(4,5-difluorobenzothiazol-2-yl)methyl]amine
N-(2-methylthiophenyl)[(5,7-difluorobenzothiazol-2-yl)methyl]amine
N-(2-methylthiophenyl)[(6,7-difluorobenzothiazol-2-yl)methyl]amine
N-(2-methylthiophenyl)[(4,5-dichlorobenzothiazol-2-yl)methyl]amine
N-(4-propylthiophenyl)[(4,5,7-trifluorobenzothiazol-2-yl)methyl]amine
N-(4-propylthiophenyl)[(4,5-difluorobenzothiazol-2-yl)methyl]amine
N-(4-propylthiophenyl)[(5,7-difluorobenzothiazol-2-yl)methyl]amine
N-(4-propylthiophenyl)[(6,7-difluorobenzothiazol-2-yl)methyl]amine
N-(4-propylthiophenyl)[(4,5-dichlorobenzothiazol-2-yl)methyl]amine
N-(2-chlorophenyl)[(4,5,7-trifluorobenzothiazol-2-yl)methyl]amine
N-(2-chlorophenyl)[(4,5-difluorobenzothiazol-2-yl)methyl]amine
N-(2-chlorophenyl)[(5,7-difluorobenzothiazol-2-yl)methyl]amine
N-(2-chlorophenyl)[(6,7-difluorobenzothiazol-2-yl)methyl]amine
N-(2-chlorophenyl)[(4,5-dichlorobenzothiazol-2-yl)methyl]amine
N-(3-chlorophenyl)[(4,5,7-trifluorobenzothiazol-2-yl)methyl]amine
N-(3-chlorophenyl)[(4,5-difluorobenzothiazol-2-yl)methyl]amine
N-(3-chlorophenyl)[(5,7-difluorobenzothiazol-2-yl)methyl]amine
N-(3-chlorophenyl)[(6,7-difluorobenzothiazol-2-yl)methyl]amine
N-(3-chlorophenyl)[(4,5-dichlorobenzothiazol-2-yl)methyl]amine
N-(4-chlorophenyl)[(4,5,7-trifluorobenzothiazol-2-yl)methyl]amine N-(4-chlorophenyl)[(4,5-difluorobenzothiazol-2-yl)methyl]amine
N-(4-chlorophenyl)[(5,7-difluorobenzothiazol-2-yl)methyl]amine
N-(4-chlorophenyl)[(6,7-difluorobenzothiazol-2-yl)methyl]amine
N-(4-chlorophenyl)[(4,5-dichlorobenzothiazol-2-yl)methyl]amine
N-(2-bromophenyl)[(4,5,7-trifluorobenzothiazol-2-yl)methyl]amine
N-(2-bromophenyl)[(4,5-difluorobenzothiazol-2-yl)methyl]amine
N-(2-bromophenyl)[(5,7-difluorobenzothiazol-2-yl)methyl]amine
N-(2-bromophenyl)[(6,7-difluorobenzothiazol-2-yl)methyl]amine
N-(2-bromophenyl)[(4,5-dichlorobenzothiazol-2-yl)methyl]amine
N-(3-bromophenyl)[(4,5,7-trifluorobenzothiazol-2-yl)methyl]amine
N-(3-bromophenyl)[(4,5-difluorobenzothiazol-2-yl)methyl]amine
N-(3-bromophenyl)[(5,7-difluorobenzothiazol-2-yl)methyl]amine
N-(3-bromophenyl)[(6,7-difluorobenzothiazol-2-yl)methyl]amine
N-(3-bromophenyl)[(4,5-dichlorobenzothiazol-2-yl)methyl]amine
N-(4-bromophenyl)[(4,5,7-trifluorobenzothiazol-2-yl)methyl]amine
N-(4-bromophenyl)[(4,5-difluorobenzothiazol-2-yl)methyl]amine
N-(4-bromophenyl)[(5,7-difluorobenzothiazol-2-yl)methyl]amine
N-(4-bromophenyl)[(6,7-difluorobenzothiazol-2-yl)methyl]amine
N-(4-bromophenyl)[(4,5-dichlorobenzothiazol-2-yl)methyl]amine
N-(2-fluorophenyl)[(4,5,7-trifluorobenzothiazol-2-yl)methyl]amine
N-(2-fluorophenyl)[(4,5-difluorobenzothiazol-2-yl)methyl]amine
N-(2-fluorophenyl)[(5,7-difluorobenzothiazol-2-yl)methyl]amine
N-(2-fluorophenyl)[(6,7-difluorobenzothiazol-2-yl)methyl]amine
N-(2-fluorophenyl)[(4,5-dichlorobenzothiazol-2-yl)methyl]amine
N-(3-fluorophenyl)[(4,5,7-trifluorobenzothiazol-2-yl)methyl]amine
N-(3-fluorophenyl)[(4,5-difluorobenzothiazol-2-yl)methyl]amine
N-(3-fluorophenyl)[(5,7-difluorobenzothiazol-2-yl)methyl]amine
N-(3-fluorophenyl)[(6,7-difluorobenzothiazol-2-yl)methyl]amine
N-(3-fluorophenyl)[(4,5-dichlorobenzothiazol-2-yl)methyl]amine
N-(4-fluorophenyl)[(4,5,7-trifluorobenzothiazol-2-yl)methyl]amine
N-(4-fluorophenyl)[(4,5-difluorobenzothiazol-2-yl)methyl]amine
N-(4-fluorophenyl)[(5,7-difluorobenzothiazol-2-yl)methyl]amine
N-(4-fluorophenyl)[(6,7-difluorobenzothiazol-2-yl)methyl]amine
N-(4-fluorophenyl)[(4,5-dichlorobenzothiazol-2-yl)methyl]amine
N-phenyl[(4,5,7-trifluorobenzothiazol-2-yl)methyl]amine
N-phenyl[(4,5-difluorobenzothiazol-2-yl)methyl]amine
N-phenyl[(5,7-difluorobenzothiazol-2-yl)methyl]amine
N-phenyl[(6,7-difluorobenzothiazol-2-yl)methyl]amine
N-phenyl[(4,5-dichlorobenzothiazol-2-yl)methyl]amine Also, the compound of the formula (IV) and salt thereof used in the aforementioned Production 2 are novel compounds and can be produced by the following method. That is, a compound of the formula (III) and a compound of the formula (VI) or a salt thereof are reacted under the reaction conditions similar to those of the aforementioned Production 1. The starting compound of the formula (III) is known or can be produced with ease by a known method.

The typical compounds of the formula (IV) which are intermediates of the present invention are exemplified by the following compounds.

ethyl N-(cyanomethyl)-N-(2-methylphenyl)succinamate
ethyl N-(cyanomethyl)-N-(3-methylphenyl)succinamate
ethyl N-(cyanomethyl)-N-(4-methylphenyl)succinamate
ethyl N-(cyanomethyl)-N-(3-ethylphenyl)succinamate
ethyl N-(cyanomethyl)-N-(3-propylphenyl)succinamate
ethyl N-(cyanomethyl)-N-(4-isopropylphenyl)succinamate
ethyl N-(4-butylphenyl)-N-(cyanomethyl)succinamate
ethyl N-(4-tert-butylphenyl)-N-(cyanomethyl)succinamate
ethyl N-(cyanomethyl)-N-(2-methoxyphenyl)succinamate
ethyl N-(cyanomethyl)-N-(3-methoxyphenyl)succinamate
ethyl N-(cyanomethyl)-N-(4-methoxyphenyl)succinamate
ethyl N-(cyanomethyl)-N-(3-ethoxyphenyl)succinamate
ethyl N-(cyanomethyl)-N-(4-propoxyphenyl)succinamate
ethyl N-(4-butoxyphenyl)-N-(cyanomethyl)succinamate
ethyl N-(cyanomethyl)-N-(2-methylthiophenyl)succinamate
ethyl N-(cyanomethyl)-N-(3-methylthiophenyl)succinamate
ethyl N-(cyanomethyl)-N-(4-methylthiophenyl)succinamate
ethyl N-(cyanomethyl)-N-(3-ethylthiophenyl)succinamate
ethyl N-(cyanomethyl)-N-(4-propylthiophenyl)succinamate
ethyl N-(4-butylthiophenyl)-N-(cyanomethyl)succinamate
ethyl N-(cyanomethyl)-N-(2-chlorophenyl)succinamate
ethyl N-(cyanomethyl)-N-(3-chlorophenyl)succinamate
ethyl N-(cyanomethyl)-N-(4-chlorophenyl)succinamate
ethyl N-(cyanomethyl)-N-(2-bromophenyl)succinamate
ethyl N-(cyanomethyl)-N-(3-bromophenyl)succinamate
ethyl N-(cyanomethyl)-N-(4-bromophenyl)succinamate
ethyl N-(cyanomethyl)-N-(2-fluorophenyl)succinamate
ethyl N-(cyanomethyl)-N-(3-fluorophenyl)succinamate
ethyl N-(cyanomethyl)-N-(4-fluorophenyl)succinamate
ethyl N-(cyanomethyl)-N-phenylsuccinamate
methyl N-(cyanomethyl)-N-(2-methylphenyl)succinamate
methyl N-(cyanomethyl)-N-(3-methylphenyl)succinamate
methyl N-(cyanomethyl)-N-(4-methylphenyl)succinamate
methyl N-(cyanomethyl)-N-(3-ethylphenyl)succinamate
methyl N-(cyanomethyl)-N-(3-propylphenyl)succinamate
methyl N-(cyanomethyl)-N-(4-isopropylphenyl)succinamate
methyl N-(4-butylphenyl)-N-(cyanomethyl)succinamate
methyl N-(4-tert-butylphenyl)-N-(cyanomethyl)succinamate
methyl N-(cyanomethyl)-N-(2-methoxyphenyl)succinamate
methyl N-(cyanomethyl)-N-(3-methoxyphenyl)succinamate
methyl N-(cyanomethyl)-N-(4-methoxyphenyl)succinamate
methyl N-(cyanomethyl)-N-(3-ethoxyphenyl)succinamate
methyl N-(cyanomethyl)-N-(4-propoxyphenyl)succinamate
methyl N-(4-butoxyphenyl)-N-(cyanomethyl)succinamate
methyl N-(cyanomethyl)-N-(2-methylthiophenyl)succinamate
methyl N-(cyanomethyl)-N-(3-methylthiophenyl)succinamate
methyl N-(cyanomethyl)-N-(4-methylthiophenyl)succinamate methyl N-(cyanomethyl)-N-(3-ethylthiophenyl)succinamate
methyl N-(cyanomethyl)-N-(4-propylthiophenyl)succinamate
methyl N-(4-butylthiophenyl)-N-(cyanomethyl)succinamate
methyl N-(cyanomethyl)-N-(2-chlorophenyl)succinamate
methyl N-(cyanomethyl)-N-(3-chlorophenyl)succinamate
methyl N-(cyanomethyl)-N-(4-chlorophenyl)succinamate
methyl N-(cyanomethyl)-N-(2-bromophenyl)succinamate
methyl N-(cyanomethyl)-N-(3-bromophenyl)succinamate
methyl N-(cyanomethyl)-N-(4-bromophenyl)succinamate
methyl N-(cyanomethyl)-N-(2-fluorophenyl)succinamate
methyl N-(cyanomethyl)-N-(3-fluorophenyl)succinamate
methyl N-(cyanomethyl)-N-(4-fluorophenyl)succinamate
methyl N-(cyanomethyl)-N-phenylsuccinamate
propyl N-(cyanomethyl)-N-(2-methylphenyl)succinamate
propyl N-(cyanomethyl)-N-(3-methylphenyl)succinamate
propyl N-(cyanomethyl)-N-(4-methylphenyl)succinamate
propyl N-(cyanomethyl)-N-(3-ethylphenyl)succinamate
propyl N-(cyanomethyl)-N-(3-propylphenyl)succinamate
propyl N-(cyanomethyl)-N-(4-isopropylphenyl)succinamate
propyl N-(4-butylphenyl)-N-(cyanomethyl)succinamate
propyl N-(4-tert-butylphenyl)-N-(cyanomethyl)succinamate
propyl N-(cyanomethyl)-N-(2-methoxyphenyl)succinamate
propyl N-(cyanomethyl)-N-(3-methoxyphenyl)succinamate
propyl N-(cyanomethyl)-N-(4-methoxyphenyl)succinamate
propyl N-(cyanomethyl)-N-(3-ethoxyphenyl)succinamate
propyl N-cyanomethyl)-N-(4-propoxyphenyl)succinamate
propyl N-4-butoxyphenyl)-N-(cyanomethyl)succinamate
propyl N-cyanomethyl)-N-(2-methylthiophenyl)succinamate
propyl N-cyanomethyl)-N-(3-methylthiophenyl)succinamate
propyl N-cyanomethyl)-N-(4-methylthiophenyl)succinamate
propyl N-cyanomethyl)-N-(3-ethylthiophenyl)succinamate
propyl N-cyanomethyl)-N-(4-propylthiophenyl)succinamate
propyl N-(4-butylthiophenyl)-N-(cyanomethyl)succinamate
propyl N-(cyanomethyl)-N-(2-chlorophenyl)succinamate
propyl N-(cyanomethyl)-N-(3-chlorophenyl)succinamate
propyl N-(cyanomethyl)-N-(4-chlorophenyl)succinamate
propyl N-(cyanomethyl)-N-(2-bromophenyl)succinamate
propyl N-(cyanomethyl)-N-(3-bromophenyl)succinamate
propyl N-(cyanomethyl)-N-(4-bromophenyl)succinamate
propyl N-(cyanomethyl)-N-(2-fluorophenyl)succinamate
propyl N-(cyanomethyl)-N-(3-fluorophenyl)succinamate
propyl N-(cyanomethyl)-N-(4-fluorophenyl)succinamate
propyl N-(cyanomethyl)-N-phenylsuccinamate The results of the pharmacological tests to show the effectiveness of the typical benzothiazole derivative of the formula (I) of the present invention are given in the following. The similar results were also obtained with regard to the compounds of the present invention that are not exemplified here.

1) Aldose reductase inhibitory action
Preparation of enzyme

An aldose reductase enzyme standard product was prepared from swine lens according to the method of S. Hayman et al. Journal of Biological Chemistry, 240, 877–882(1965)]. That is, swine lenses freeze-stored at −80° C. were homogenized with distilled water and cetrifuged at 10,000 G for 15 minutes. The supernatant was prepared into a 40% ammonium sulfate solution and subjected to cetrifugation at 10,000 G for 10 minutes. The supernatant obtained was dialyzed overnight against a 0.05M sodium chloride solution to give a dialyzed solution, which was used as an enzyme standard product.

Activity determination

Test drugs: Compound of the invention and EPALRESTAT (described in Japanese Patent Unexamined Publication No. 40478/1982)

The activity of aldose reductase was determined by the above-mentioned method of S. Hayman et al. That is, the above-mentioned enzyme solution (25 μl) and a drug solution (25 μl) dissolved in 1% DMSO at various concentrations were added to a 40 mM phosphate buffer (200 μl, pH 6.2) containing final concentrations of 0.4 M lithium sulfate, 0.1 mM NADPH (reduced type nicotinamide adenine dinucleotide phosphate) and 3 mM dl-glyceraldehyde as a substrate. The mixture was allowed to react at 25° C. for 2 minutes and the changes in absorbance at 340 nm were determined with COBAS FARA II (manufactured by Roche).

The changes in absorbance when 1% DMSO was added instead of the drug solution was taken as 100%, based on which 50% inhibition concentration ($IC_{50}$) was calculated and shown in Table 1.

In the Table, $IC_{50}$ (M) shows the concentration of the compound of the present invention inhibiting the aldose reductase activity by 50%. The test drug number indicates the example number to be mentioned later.

TABLE 1

| Test drug | $IC_{50}$ (M) |
| --- | --- |
| Example 39 | $1.3 \times 10^{-8}$ |
| Example 41 | $1.3 \times 10^{-8}$ |
| Example 65 | $1.5 \times 10^{-8}$ |
| Example 72 | $1.3 \times 10^{-8}$ |
| EPALRESTAT | $2.1 \times 10^{-8}$ |

[1] Japanese Patent Unexamined Publication No. 40478/1982

2) Inhibitory action on sorbitol accumulation in tissues of rats with experimental diabetes Test Drugs: Compound of the invention and EPALRESTAT (described in Japanese Patent Unexamined Publication No. 40478/1982)

Sprague-Dawley rats (male, 6 weeks old, 5–6 per group) were fasted for 18 hours and injected with streptozotocin (SIGMA, 60 mg/kg) via the tail vein under etherization to prepare rats with diabetes.

The various compounds were orally administered at 4, 8 and 24 hours after the injection of streptozotocin, at 10 mg/kg or 30 mg/kg as a 0.5% carboxymethylcellulose suspension. During the administrations, the rats were raised under free access to feed and water and the sorbitol content in the tissues (erythrocytes, sciatic nerve, lens) was determined 3 hours after the final administration, according to the enzyme method of H. Y. Bergmeyer et al. [Methods of Enzymatic Analysis, vol. 3, 1323–1330 (1974)] with the use of SDH (sorbitol dehydrogenase) and NAD (β-nicotinamide adenine dinucleotide). The results are expressed in percent (%) relative to the value of a control group administered with 0.5% carboxymethylcellulose solution (solvent) instead of the compound, which was taken as 100%. The results are shown in Table 2.

TABLE 2

| Test drug | Sorbitol accumulation (%)[1] | | |
|---|---|---|---|
| | erythrocytes | sciatic nerve | lens |
| Example 37[a] | 16.4** | 17.8** | 55.4** |
| Example 48[a] | 32.8** | 45.7** | 56.6* |
| Example 55[a] | 2.5** | 27.2** | 74.4* |
| Example 65[a] | 6.4** | 4.0** | 71.8* |
| Example 72[a] | 19.2** | 10.8** | 50.0** |
| EPALRESTAT[b] | 66.5 | 99.9 | 89.1 |

[1] The control was taken as 100%.
Tukey's Multiple Range Test:
* $p<0.05$
** $p<0.01$
[a] 10 mg/kg
[b] 30 mg/kg The acute toxicity (safety) of the compound of the present invention was confirmed by the following method.

Normal ICR mice (male, 7 weeks old, 5 per group) were fasted for 18 hours and the compound (300 mg/kg) of Example 37 was orally administered as a 0.5% carboxymethylcellulose suspension. To the control group, a 0.5% carboxymethylcellulos e solution alone was orally administered and observation was continued for 14 days thereafter, during which period the mice were allowed to take feed and water freely.

As a result, there was no case of death among the mice administered with the compound of Example 37 and their weights showed transition in the same manner as in the control group.

The compound of the present invention has a superior aldose reductase inhibitory action on mammals inclusive of human, cow, horse, dog, mouse, rat and so on and shows superior safety. Accordingly, it is effectively used for the prevention and/or treatment of the complications of diabetes, such as faulty union of corneal injury, diabetic neurosis, nephropathy, retinopathy and cataract. When the compound of the present invention is administered for the prevention and/or treatment of the above-mentioned diseases, oral or parenteral administration can be employed.

The pharmaceutical composition containing the compound of the present invention is provided in the form of a solid preparation, semi-solid preparation or liquid preparation together with organic or inorganic carrier and/or excipient suitable for external, oral or local administration. The compound of the present invention is prepared into a dosage form such as tablet, pellet, capsule, suppository, liquid, emulsion or suspension along with nontoxic and pharmacologically acceptable auxiliary ingredients. The auxiliary ingredients include those effectively used for the production of solid, semi-solid or liquid preparation, such as water, glucose, lactose, gelatin, mannitol, starch paste, magnesium trisillicate, corn starch, keratin, colloidal silica, potato starch and urea. The auxiliary ingredients include stabilizer, extender, coloring and aromatic agent. So as to retain the activity of the compound of the present invention, a preservative may be also contained. The pharmaceutical preparation should contain the compound of the present invention in an amount sufficient to produce the desired therapeutic effect against the progress or symptom of the target diseases.

When the compound of the present invention is administered to human, it is administered, for example, parenterally (preferably by injection or eye drop) or orally in an amount sufficient to inhibit aldose reductase or an amount sufficient to prevent and/or treat the complications of diabetes. While the effective amount of the compound of the present invention varies depending on age, body weight, symptom, therapeutic effect, administration route, administration period etc., it is generally administered orally at 1–2000 mg/day, preferably at 10–600 mg/day in a single to thrice divided doses a day.

The pharmaceutical composition of the present invention contains the compound of the present invention and is effective as an aldose reductase inhibitor and for the prevention and/or treatment of the complications of diabetes, such as faulty union of corneal injury, diabetic neurosis, nephropathy, retinopathy and cataract as mentioned above.

An administration of the compound of the present invention in an effective amount to mammals such as human results in inhibition of aldose reductase activity, which ultimately results in the prevention and/or treatment of the complications of diabetes, such as faulty union of corneal injury, diabetic neurosis, nephropathy, retinopathy and cataract.

The present invention is explained in more detail in the following by way of examples, to which the present invention is not limited.

EXAMPLE 1

Production of methyl N-(4-chlorophenyl)-N-[(4,5,7-trifluorobenzothiazol- 2-yl)methyl]succinamate N-(4-Chlorophenyl)[(4,5,7-trifluorobenzothiazol-2-yl)methyl]amine (300 mg) and triethylamine (110 mg) were dissolved in dichloromethane (5 ml) and the mixture was cooled with ice. Methylsuccinyl chloride (165 mg) was dropwise added and the mixture was stirred under an argon atmosphere for 1.5 hours. A saturated aqueous solution of ammonium chloride was added to the reaction mixture and the mixture was extracted with ethyl acetate. The organic layer was washed with a saturated aqueous solution of sodium chloride and dried over anhydrous sodium sulfate, followed by evaporation of the solvent.

The obtained oily residue was subjected to silica gel chromatography and eluted with dichloromethane-ethyl acetate to give 190 mg of the title compound. The structural formula and physical properties of the obtained compound are given in Table 3.

EXAMPLES 2–17

In substantially the same manner as in Example 1, the compounds shown in Table 3 and Table 4 were obtained. The structural formulas and physical properties of the obtained compounds are shown in Table 3 and Table 4.

EXAMPLE 18

Production of ethyl N-[(6,7-difluorobenzothiazol-2-yl)methyl]-N-( 4-methoxyphenyl)succinamate Ethyl N-(cyanomethyl)-N-(4-methoxyphenyl)succinamate (260 mg) and 2-amino-5,6-difluorothiophenol hydrochloride (196 mg) were refluxed under heating in absolute ethanol (5 ml) under an argon atmosphere. Fifteen hours later, the solvent was distilled away. To the residue was added water and the mixture was extracted with ethyl acetate. The organic layer was dried over anhydrous sodium sulfate and the solvent was distilled away. The obtained oily substance was subjected to silica gel chromatography and eluted with dichloromethane-ethyl acetate to give 230 mg of the title compound. The structural formula and physical properties of the obtained compound are shown in Table 4.

TABLE 3

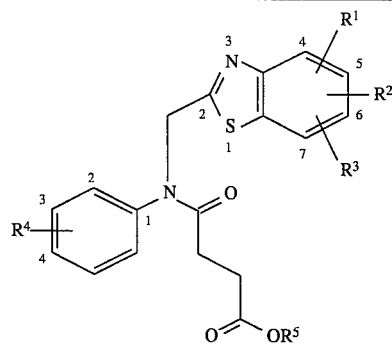

| Ex. No. | $R^1, R^2, R^3$ | $R^4$ | $R^5$ | NMR (CDCl$_3$) δ in ppm scale | MS (m/z) |
|---|---|---|---|---|---|
| 1 | 4,5,7-F | 4-Cl | Me | 2.41~2.46(2H), 2.66~2.71(2H), 3.69(3H, s), 5.25(2H, s), 7.00~7.43(5H) | 443, 445 (CI) |
| 2 | 4,5-Cl | 4-Me | Me | 2.35(3H, s), 2.42~2.48(2H), 2.64~2.69 (2H), 3.68(3H, s), 5.29(2H, s), 7.14~7.24 (4H), 7.45(1H, d), 7.69(1H, d) | 437 (CI) |
| 3 | 4,5-Cl | 4-Cl | Me | 2.41~2.45(2H), 2.65~2.70(2H), 3.69(3H, s), 5.28(2H, s), 7.25~7.40(4H), 7.47(1H, d), 7.69(1H, d) | 457, 459 (CI) |
| 4 | 4,5,7-F | 4-F | Me | 2.43~2.48(2H), 2.67~2.72(2H), 3.69(3H, s), 5.27(2H, s), 7.02~7.36(5H) | 427 (CI) |
| 5 | 4,5,7-F | 4-Me | Me | 2.36(3H, s), 2.43~2.48(2H), 2.64~2.69 (2H), 3.69(3H, s), 5.25(2H, s), 7.13~7.26(5H) | 423 (CI) |
| 6 | 4,5-F | 3-F | Et | 1.24(3H, t), 2.43~2.48(2H), 2.63~2.68 (2H), 4.13(2H, q), 5.27(2H, s), 7.01~7.57(6H) | 422 (EI) |
| 7 | 5,7-F | 3-F | Et | 1.24(3H, t), 2.43~2.48(2H), 2.65~2.69(2H), 4.14(2H, q), 5.23(2H, s), 6.88~7.49(6H) | 422 (EI) |
| 8 | 4,5,7-F | 3-F | Et | 1.26(3H, t), 2.42~2.48(2H, 2.64~2.69 (2H), 4.13(2H, q), 5.25(2H, s), 6.97~7.44(5H) | 440 (EI) |
| 9 | 4,5,7-F | 4-Br | Et | 1.26(3H, t), 2.41~2.75(4H), 4.12(2H, q), 5.23(2H, s), 7.01~7.09(1H), 7.18(2H, d), 7.55(2H, d) | 503, 501 (CI) |

TABLE 4

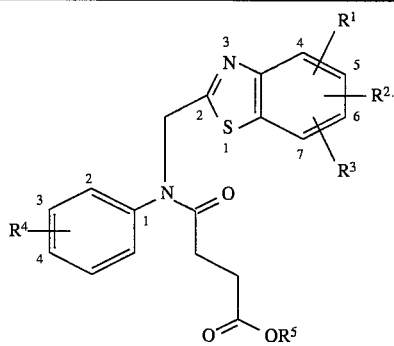

| Ex. No. | $R^1, R^2, R^3$ | $R^4$ | $R^5$ | NMR (CDCl$_3$) δ in ppm scale | MS (m/z) |
|---|---|---|---|---|---|
| 10 | 4,5,7-F | 2-OMe | Et | 1.25(3H, t), 2.25~2.72(4H), 3.77(3H, s), 4.13(2H, q), 4.87(1H, d), 5.50(1H, d), 6.92~7.35(5H) | 453 (CI) |
| 11 | 4,5,7-F | 2-F | Et | 1.26(3H, t), 2.37~2.76(4H), 4.14(2H, q), 5.03(1H, d), 5.47(1H, d), 6.99~7.43(2H) | 441 (CI) |
| 12 | 4,5,7-F | 2-Cl | Et | 1.26(3H, t), 2.64~2.93(4H), 4.11(2H, q), | 457, 459 |

TABLE 4-continued

| Ex. No. | $R^1,R^2,R^3$ | $R^4$ | $R^5$ | NMR (CDCl$_3$) δ in ppm scale | MS (m/z) |
|---|---|---|---|---|---|
| | | | | 4.76(1H, d), 5.72(1H, d), 7.02~7.55(5H) | (CI) |
| 13 | 4,5,7-F | 3-Cl | Et | 1.25(3H, t), 2.41~2.81(4H), 4.14(2H, q), 5.21(1H, d), 5.40(1H, d), 7.00~7.43(5H) | 457, 459 (CI) |
| 14 | 4,5-F | 3-Cl | Et | 1.25(3H, t), 2.44~2.70(4H), 4.14(2H, q), 5.27(2H, s), 7.20~7.58(6H) | 439, 441 (CI) |
| 15 | 4,5-Cl | 3-Cl | Et | 1.25(3H, t), 2.44~2.69(4H), 4.17(2H, q), 5.29(2H, s), 7.23~7.71(6H) | 472, 474 (CI) |
| 16 | 4,5,7-F | 4-iso propyl | Et | 1.18~1.28(9H), 2.45~2.74(4H), 2.90~2.97(1H), 4.14(2H, q), 5.27(2H, s), 7.00~7.09(1H, 7.18(2H, d), 7.26(2H, d) | 465 (CI) |
| 17 | 5,7-F | 2-OMe | Et | 1.25(3H, t), 2.22~2.75(4H), 3.76(3H, s), 4.14(2H, q), 4.81(1H, d), 5.52(1H, d), 6.87~7.46(6H) | 435 (CI) |
| 18 | 6,7-F | 4-OMe | Et | 1.26(3H, t), 2.41~2.46(2H), 2.63~2.68 (2H), 3.80(3H, s), 4.14(2H, q), 5.21(2H, s), 6.87~7.70(6H) | 435 (CI) |

EXAMPLES 19–36

In substantially the same manner as in Example 18, the compounds shown in Table 5 and Table 6 were obtained. The structural formulas and physical properties of the obtained compounds are shown in Table 5 and Table 6.

TABLE 5

| Ex. No. | $R^1,R^2,R^3$ | $R^4$ | $R^5$ | NMR (CDCl$_3$) δ in ppm scale | MS (m/z) |
|---|---|---|---|---|---|
| 19 | 4,5,7-F | 4-OMe | Et | 1.26(3H, t), 2.42~2.47(2H), 2.64~2.68(2H), 3.81(3H, s), 4.14(2H, q) 5.25(2H, s), 6.89~7.21(5H) | 453 (CI) |
| 20 | 6,7-F | 4-F | Et | 1.26(3H, t), 2.38~2.43(2H), 2.64~2.69 (2H), 4.13(2H, q), 5.21(2H, s), 7.06~7.70 (6H) | 423 (CI) |
| 21 | 5,7-F | 4-F | Et | 1.26(3H, t), 2.39~2.43(2H), 2.64~2.69 | 423 |

TABLE 5-continued

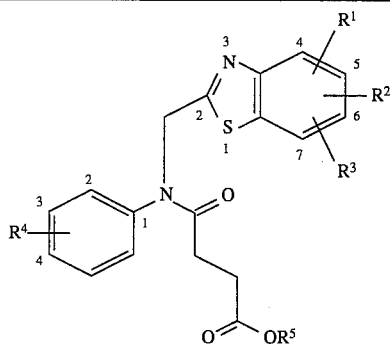

| Ex. No. | $R^1,R^2,R^3$ | $R^4$ | $R^5$ | NMR (CDCl$_3$) δ in ppm scale | MS (m/z) |
|---|---|---|---|---|---|
| | | | | (2H), 4.12(2H, q), 5.23(2H, s), 6.90~7.49(6H) | (CI) |
| 22 | 4,5-F | 4-Cl | Et | 1.25(3H, t), 2.40~2.45(2H), 2.64~2.69 (2H), 4.14(2H, q), 5.26(2H, s), 7.21~7.57(6H) | 439, 441 (CI) |
| 23 | 5,7-F | 4-Cl | Et | 1.26(3H, t), 2.40~2.45(2H), 2.64~2.69 (2H), 4.12(2H, q), 5.23(2H, s), 6.90~7.49(6H) | 439, 441 (CI) |
| 24 | 5,7-F | 4-Me | Et | 1.25(3H, t), 2.36(3H, s), 2.42~2.47(2H), 2.62~2.68(2H), 4.14(2H, q), 5.23(2H, s), 6.88~7.48(6H) | 419 (CI) |
| 25 | 5,7-F | 3-OMe | Et | 1.25(3H, t), 2.47~2.52(2H), 2.64~2.69(2H), 3.78(2H, s), 4.14(2H, q), 5.25(2H, s), 6.94~7.49(6H) | 435 (CI) |
| 26 | 4,5,7-F | 3-OMe | Et | 1.26(3H, s), 2.47~2.52(2H), 2.64~2.69 (2H), 3.80(3H, s), 4.14(2H, q), 5.26(2H, s), 6.84~7.34(5H) | 453 (CI) |
| 27 | 4,5,7-F | 3-Et | Et | 1.19~1.28(6H), 2.44~2.49(2H), 2.61~2.69(4H), 4.14(2H, q), 5.27(2H, s), 6.99~7.34(5H) | 451 (CI) |
| 28 | 4,5,7-F | 2-Me | Et | 1.26(3H, t), 2.18~2.70(4H), 2.27(3H, s), 4.15(2H, q), 4.72(1H, d), 5.63(1H, d), 7.00~7.35(5H) | 437 (CI) |

TABLE 6

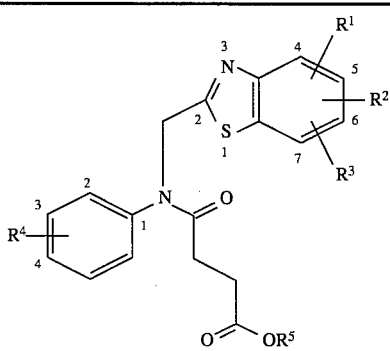

| Ex. No. | $R^1,R^2,R^3$ | $R^4$ | $R^5$ | NMR (CDCl$_3$) δ in ppm scale | MS (m/z) |
|---|---|---|---|---|---|
| 29 | 4,5,7-F | H | Me | 2.43~2.48(2H, 2.64~2.70(2H), 3.69(3H, s), 5.28(2H, s), 6.99~7.46(6H) | 409 (CI) |
| 30 | 4,5-F | H | Et | 1.25(3H, t), 2.42~2.47(2H), 2.63~2.68(2H), 4.14(2H, q), 5.29(2H, s), 7.20~7.57(7H) | 404 (EI) |
| 31 | 5,7-F | H | Et | 1.25(3H, t), 2.42~2.47(2H), 2.64~2.69 (2H), 4.14(2H, q), 5.26(2H, s), 6.89~7.49(7H) | 404 (EI) |
| 32 | 6,7-F | H | Et | 1.26(3H, t), 2.42~2.47(2H), 2.64~2.69 (2H), 4.14(2H, q), 5.25(2H, s), | 404 (EI) |

TABLE 6-continued

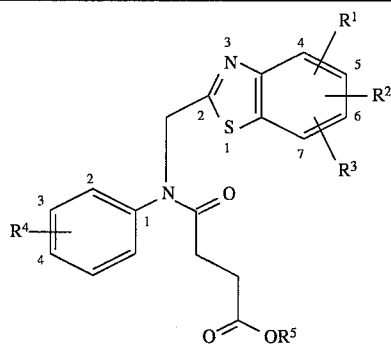

| Ex. No. | R¹,R²,R³ | R⁴ | R⁵ | NMR (CDCl₃) δ in ppm scale | MS (m/z) |
|---|---|---|---|---|---|
| 33 | 4,5-Cl | H | Et | 7.24–7.69(7H)<br>1.26(3H, t), 2.42–2.47(2H), 2.64–2.68 (2H), 4.14(2H, q), 5.31(2H, s), 7.28–7.43(5H), 7.46(1H, d), 7.69(1H, d) | 438, 436 (EI) |
| 34 | 4,5-F | 3-Me | Et | 1.25(3H, t), 2.34(3H, s), 2.43–2.48(2H), 2.63–2.68(2H), 4.14(2H, q), 5.27(2H, s), 7.03–7.57(6H) | 418 (EI) |
| 35 | 4,5,7-F | 3-Me | Et | 1.26(3H, t), 2.36(3H, s), 2.44–2.49(2H), 2.63–2.68(2H), 4.14(2H, q), 5.26(2H, s), 6.99–7.31(5H) | 436 (EI) |
| 36 | 4,5,7-F | 2-SCH₃ | Et | 1.25(3H, t), 2.25–2.81(4H, 2.46(3H, s), 4.14(2H, q), 4.68(1H, d), 5.69(1H, d), 6.99–7.41(5H) | 468 (EI) |

EXAMPLE 37

Production of N-(4-chlorophenyl)-N-[(4,5,7-trifluorobenzothiazol- 2-yl)methyl]succinamic acid The title compound (190 mg) of Example 1 was dissolved in a mixture of methanol (0.8 ml), dioxane (1.6 ml) and an aqueous solution of 2%(w/v) sodium hydroxide (1.4 ml) and the mixture was stirred at room temperature for 1 hour.

The reaction mixture was diluted with water and made acidic with hydrochloric acid, followed by extraction with ethyl acetate. The organic layer was dried over anhydrous sodium sulfate and the solvent was distilled away. To the residue was added toluene for crystallization to give 100 mg of the title compound. The structural formula and physical properties of the obtained compound are shown in Table 7.

EXAMPLES 38–72

In substantially the same manner as in Example 37, the compounds shown in Tables 7-10 were obtained. The structural formulas and physical properties of the compounds obtained in these examples are shown in Tables 7-10.

TABLE 7

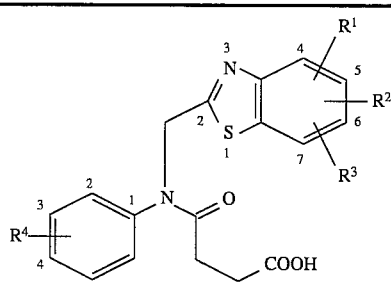

| Ex. No. | R¹,R²,R³ | R⁴ | NMR (CDCl₃) δ in ppm scale | IR(KBr) (cm⁻¹) | MS (m/z) |
|---|---|---|---|---|---|
| 37 | 4,5,7-F | 4-Cl | 2.42–2.46(2H), 2.70–2.75(2H), 5.25(2H, s), 7.00–7.42(5H) | 2620–3500, 1710, 1640 | 429, 431 (CI) |
| 38 | 4,5-Cl | 4-Me | 2.35(3H, s), 2.44–2.48(2H), 2.68–2.72 (2H), 5.29(2H, s), 7.12–7.21(4H), 7.45(1H, d), 7.69(1H, d) | 2600–3450, 1710, 1650 | 423 (CI) |
| 39 | 4,5-Cl | 4-Cl | 2.42–2.60(2H), 2.70–2.74(2H), 5.28(2H, s), 7.24–7.72(6H) | 2600–3500, 1710, 1650 | 443, 445 (CI) |
| 40 | 4,5,7-F | 4-F | 2.41–2.45(2H), 2.70–2.75(2H) 5.25(2H, s), 7.08–7.30(5H) | 2620–3450, 1710, 1650 | 413 (CI) |
| 41 | 4,5,7-F | 4-Me | 2.36(3H, s), 2.44–2.49(2H), 2.68–2.73 | 2600–3400, | 409 |

TABLE 7-continued

[Structure: benzothiazole-CH2-N(phenyl-R4)-C(=O)-CH2CH2-COOH, with R1, R2, R3 on benzothiazole positions 4,5,6,7 and R4 on phenyl]

| Ex. No. | R¹,R²,R³ | R⁴ | NMR (CDCl₃) δ in ppm scale | IR(KBr) (cm⁻¹) | MS (m/z) |
|---|---|---|---|---|---|
| | | | (2H), 5.26(2H, s), 6.99~7.26(5H) | 1710, 1640 | (CI) |
| 42 | 4,5-F | 3-F | 2.46~2.51(2H), 2.70~2.75(2H), 5.27(2H, s), 7.03~7.59(6H) | 2600~3480, 1710, 1650 | 394 (EI) |
| 43 | 5,7-F | 3-F | 2.36~2.41(2H), 2.61~2.66(2H), 5.15(2H, s), 6.81~7.41(6H) | 2610~3450, 1710, 1650 | 394 (EI) |
| 44 | 4,5,7-F | 3-F | 2.45~2.50(2H), 2.71~2.76(2H), 5.27(2H, s), 7.02~7.45(5H) | 2600~3430, 1710, 1650 | 412 (EI) |
| 45 | 4,5,7-F | 4-Br | 2.42~2.75(4H), 5.25(2H, s), 7.00~7.09 (1H), 7.18(2H, d), 7.56(2H, d) | 2700~3600, 1710, 1640 | 473, 475 (CI) |
| 46 | 4,5,7-F | 2-OMe | 2.26~2.75(4H), 3.76(3H, s), 4.87(1H, d), 5.51(1H, d), 6.92~7.39(5H) | 2800~3070, 1710, 1670 | 425 (CI) |

TABLE 8

[Structure: benzothiazole-CH2-N(phenyl-R4)-C(=O)-CH2CH2-COOH, with R1, R2, R3 on benzothiazole positions 4,5,6,7 and R4 on phenyl]

| Ex. No. | R¹,R²,R³ | R⁴ | NMR (CDCl₃) δ in ppm scale | IR(KBr) (cm⁻¹) | MS (m/z) |
|---|---|---|---|---|---|
| 47 | 4,5,7-F | 2-F | 2.34~2.85(4H), 5.01(1H, d), 5.49(1H, d), 6.99~7.44(4H) | 2510~3400, 1710, 1660 | 413 (CI) |
| 48 | 4,5,7-F | 2-Cl | 2.26~2.85(4H), 4.75(1H, d), 5.68(1H, d), 7.01~7.41(4H), 7.54(1H, d) | 2600~3400, 1710, 1660 | 429, 431 (CI) |
| 49 | 4,5,7-F | 3-Cl | 2.44~2.75(4H), 5.26(2H, s), 7.00~7.39(5H) | 2660~3450, 1710, 1650 | 429, 431 (CI) |
| 50 | 4,5-F | 3-Cl | 2.44~2.75(4H), 5.27(2H, s), 7.14~7.59(6H) | 2700~3350, 1710, 1650 | 411, 413 (CI) |
| 51 | 4,5-Cl | 3-Cl | 2.41~2.72(4H), 5.25(2H, s), 7.18~7.35 (4H), 7.43(1H, d), 7.67(1H, d) | 2700~3700, 1710, 1650 | 443, 445 (CI) |
| 52 | 4,5,7-F | 4-isopropyl | 1.26(3H, s), 1.29(3H, s), 2.45~2.74(4H), 2.87~2.99(1H), 5.26(2H, s), 6.99~7.04 (1H), 7.16(2H, d), 7.27(2H, d) | 2900~3500, 1715, 1670 | 437 (CI) |
| 53 | 5,7-F | 2-OMe | 2.28~2.74(4H), 3.76(3H, s), 4.81(1H, d), 5.53(1H, d), 6.88~7.47(6H) | 2500~3450, 1710, 1660 | 407 (CI) |
| 54 | 6,7-F | 4-OMe | 2.43~2.48(2H), 2.68~2.73(2H), 3.80(3H, s), 5.22(2H, s), 6.88~7.71(6H) | 2550~3450, 1710, 1660 | 407 (CI) |
| 55 | 4,5,7-F | 4-OMe | 2.43~2.48(2H), 2.68~2.73(2H), 3.81(3H, s), 5.25(2H, s), 6.89~7.18(5H) | 2620~3450, 1710, 1650 | 425 (CI) |
| 56 | 6,7-F | 4-F | 2.40~2.45(2H), 2.70~2.75(2H), 5.22(2H, s), 7.06~7.71(6H) | 2600~3450, 1710, 1650 | 395 (CI) |

TABLE 9

| Ex. No. | $R^1, R^2, R^3$ | $R^4$ | NMR (CDCl$_3$) δ in ppm scale | IR(KBr) (cm$^{-1}$) | MS (m/z) |
|---|---|---|---|---|---|
| 57 | 5,7-F | 4-F | 2.36~2.45(2H), 2.70~2.74(2H), 5.23(2H, s), 6.90~7.50(6H) | 2600~3450, 1710, 1650 | 395 (CI) |
| 58 | 4,5-F | 4-Cl | 2.42~2.46(2H), 2.69~2.74(2H), 5.26(2H, s), 7.21~7.58(6H), | 2600~3500, 1710, 1650 | 411, 413 (CI) |
| 59 | 5,7-F | 4-Cl | 2.42~2.46(2H), 2.70~2.75(2H), 5.23(2H, s), 6.90~7.50(6H) | 2600~3450, 1710, 1640 | 411, 413 (CI) |
| 60 | 5,7-F | 4-Me | 2.36(3H, s), 2.44~2.49(2H), 2.68~2.72(2H), 5.24(2H, s), 6.88~7.49(6H) | 2600~3450, 1710, 1640 | 391 (CI) |
| 61 | 5,7-F | 3-OMe | 2.49~2.54(2H), 2.69~2.74(2H), 3.78(3H, s), 5.25(2H, s), 6.82~7.50(6H) | 2580~3450, 1710, 1650 | 407 (CI) |
| 62 | 4,5,7-F | 3-OMe | 2.48~2.53(2H), 2.69~2.74(2H), 3.79(3H, s), 5.27(2H, s), 6.82~7.35(5H) | 2600~3450, 1710, 1650 | 425 (CI) |
| 63 | 4,5,7-F | 3-Et | 1.21(3H, t), 2.45~2.50(2H), 2.61~2.73(4H), 5.27(2H, s), 6.99~7.35(5H) | 2600~3450, 1710, 1650 | 423 (CI) |
| 64 | 4,5,7-F | 2-Me | 2.19~2.74(4H), 2.23(3H, s), 4.71(1H, d) 5.65(1H, d), 6.99~7.32(5H) | 2570~3400, 1710, 1650 | 409 (CI) |
| 65 | 4,5,7-F | H | 2.43~2.48(2H), 2.69~2.74(2H), 5.29(2H, s), 6.99~7.46(6H) | 2620~3450, 1710, 1650 | 395 (CI) |
| 66 | 4,5-F | H | 2.44~2.49(2H), 2.69~2.73(2H), 5.26(2H, s), 6.88~7.50(7H) | 2620~3100, 1710, 1650 | 376 (CI) |

TABLE 10

| Ex. No. | $R^1, R^2, R^3$ | $R^4$ | NMR (CDCl$_3$) δ in ppm scale | IR(KBr) (cm$^{-1}$) | MS (m/z) |
|---|---|---|---|---|---|
| 67 | 5,7-F | H | 2.44~2.48(2H), 2.69~2.73(2H), 5.29(2H, s), 7.21~7.58(7H) | 2600~3070, 1710, 1650 | 376 (EI) |
| 68 | 6,7-F | H | 2.43~2.48(2H), 2.69~2.73(2H), 5.25(2H, s), 7.24~7.70(7H) | 2550~3470, 1730, 1670 | 376 (EI) |
| 69 | 4,5-Cl | H | 2.44~2.49(2H), 2.69, ~2.74(2H), 5.31(2H, s), 7.27~7.47(6H), 7.55(1H, d) | 2620~3450, 1710, 1650 | 410 (EI) |
| 70 | 4,5-F | 3-Me | 2.35(3H, s), 2.45~2.49(2H), 2.68~2.73 (2H), 5.27(2H, s), 7.02~7.58(6H) | 2600~3450, 1715, 1650 | 390 (EI) |
| 71 | 4,5,7-F | 3-Me | 2.36(3H, s), 2.46~2.50(2H), 2.69~2.73 (2H), 5.27(2H, s), 6.99~7.32(5H) | 2620~3450, 1715, 1650 | 408 (EI) |
| 72 | 4,5,7-F | 2-SCH$_3$ | 2.26~2.86(4H), 2.46(3H, s), 4.67(1H, d), 5.70(1H, d), 6.99~7.42(5H) | 2680~3070, 1710, 1670 | 440 (EI) |

EXAMPLE 73

Production of N-(4-chlorophenyl)[(4,5,7-trifluorobenzothiazol-2yl)methyl]amine 2-(4-Chlorophenyl)acetonitrile (1 g) and 2-amino-3,4,6-trifluorothiophenol hydrochloride (1.29 g) in absolute ethanol (25 ml) were refluxed under heating under an argon atmosphere. Fifteen hours later, the solvent was distilled away. To the residue was added water and the mixture was extracted with ethyl acetate. The organic layer was dried over anhydrous sodium sulfate and the solvent was distilled away. The obtained oily substance was subjected to silica gel chromatography and eluted with dichloromethane-ethyl acetate to give 680 mg of the title compound. The structural formula and physical properties of the obtained compound are shown in Table 11.

EXAMPLES 74–89

In substantially the same manner as in Example 73, the compounds shown in Table 11 and Table 12 were obtained. The structural formulas and physical properties of the obtained compounds are shown in Table 11 and Table 12.

TABLE 11

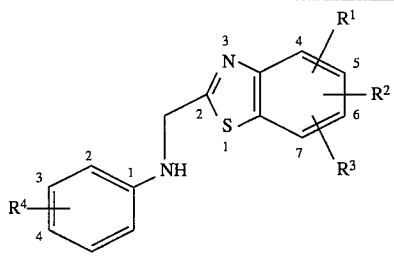

| Ex. No. | $R^1,R^2,R^3$ | $R^4$ | NMR (CDCl$_3$) δ in ppm scale | MS (m/z) |
|---|---|---|---|---|
| 73 | 4,5,7-F | 4-Cl | 4.78~4.83(2H, bs), 6.57~7.24(5H) | 329, 331 (CI) |
| 74 | 4,5-Cl | 4-Me | 2.24(3H, s), 4.78~4.82(2H), 6.64(2H, d), 7.02(2H, d), 7.44(1H, d), 7.64(1H, d) | 323 (CI) |
| 75 | 4,5-Cl | 4-Cl | 4.77~4.80(2H), 6.56~7.15(4H), 7.43(1H, d), 7.62(1H, d) | 342, 344 (CI) |
| 76 | 4,5,7-F | 4-F | 4.71(2H, s), 6.51~7.06(5H) | 313 (CI) |
| 77 | 4,5,7-F | 4-Me | 2.22(3H, s), 4.76~4.81(2H), 6.55~7.23(5H) | 309 (CI) |
| 78 | 4,5-F | 3-F | 4.75(2H, s), 6.38~7.55(6H) | 294 (EI) |
| 79 | 5,7-F | 3-F | 4.78(2H, s), 6.38~7.54(6H) | 294 (EI) |
| 80 | 4,5,7-F | 3-F | 4.78(2H, s), 6.35~7.18(5H) | 312 (EI) |
| 81 | 4,5,7-F | 4-Br | 4.76(2H, s), 6.56(2H, d), 6.99~7.07(1H), 7.28(2H, d) | 373, 375 (CI) |

TABLE 12

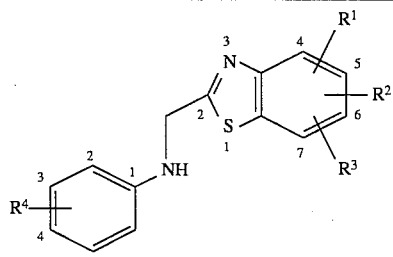

| Ex. No. | $R^1,R^2,R^3$ | $R^4$ | NMR (CDCl$_3$) δ in ppm scale | MS (m/z) |
|---|---|---|---|---|
| 82 | 4,5,7-F | 2-OMe | 3.87(3H, s), 4.78(2H, s), 6.95~7.50(5H) | 325 (CI) |
| 83 | 4,5,7-F | 2-F | 4.84(2H, s), 6.52~7.31(5H) | 313 (CI) |

TABLE 12-continued

| Ex. No. | R¹,R²,R³ | R⁴ | NMR (CDCl$_3$) δ in ppm scale | MS (m/z) |
|---|---|---|---|---|
| 84 | 4,5,7-F | 2-Cl | 4.86(2H, s), 6.51~7.33(5H) | 329, 331 (CI) |
| 85 | 4,5,7-F | 3-Cl | 4.79(2H, bs), 6.45~7.30(5H) | 329, 331 (CI) |
| 86 | 4,5-F | 3-Cl | 4.78(2H, d), 6.55~7.55(6H) | 311, 313 (CI) |
| 87 | 4,5-Cl | 3-Cl | 4.80(2H, d), 6.58~7.60(6H) | 343, 345 (CI) |
| 88 | 4,5,7-F | 4-iso propyl | 1.18(3H, s), 1.21(3H, s), 2.78~2.83(1H), 4.77(2H), 6.63(2H, d), 6.96~7.08(1H), 7.07(2H, d) | 337 (CI) |
| 89 | 5,7-F | 2-OMe | 3.88(3H, s), 4.76(2H, s), 6.54~7.52(6H) | 307 (CI) |

EXAMPLE 90

Production of ethyl N-(cyanomethyl)-N-(4-methylphenyl)succinamate 2-(4-Methylphenylamino)acetonitrile (600 mg) and triethylamine (548 mg) were dissolved in dichloromethane (10 ml) and the mixture was cooled with ice. Ethylsuccinyl chloride (882 mg) was dropwise added and the mixture was stirred under an argon atmosphere for 3.5 hours. A saturated aqueous solution of ammonium chloride was added and the mixture was extracted with ethyl acetate. The organic layer was washed with a saturated aqueous solution of sodium chloride and dried over anhydrous sodium sulfate, followed by evaporation of the solvent.

The obtained oily residue was subjected to silica gel chromatography and eluted with dichloromethane-ethyl acetate to give 770 mg of the title compound. The structural formula and physical properties of the obtained compound are shown in Table 13.

EXAMPLES 91–100

In substantially the same manner as in Example 90, the compounds shown in Table 13 were obtained. The structural formulas and physical properties of the obtained compounds are shown in Table 13.

TABLE 13

| Ex. No. | R⁴ | R⁵ᵃ | NMR (CDCl$_3$) δ in ppm scale | MS (m/z) |
|---|---|---|---|---|
| 90 | 4-Me | Et | 1.25(3H, t), 2.34~2.41(5H), 2.58~2.64 (2H), 4.13(2H, q), 4.58(2H, s), 7.21~7.33(4H) | 275 (CI) |
| 91 | 4-F | Et | 1.25(3H, t), 2.31~2.35(2H), 2.58~2.64 (2H), 4.14(2H, q), 4.58(2H, s), 7.18~7.42(4H) | 279 (CI) |
| 92 | 4-Cl | Et | 1.26(3H, t), 2.32~2.38(2H), 2.59~2.66 (2H), 4.14(2H, q), 4.58(2H, s), 7.31~7.54(4H) | 295, 297 (CI) |
| 93 | 4-OMe | Et | 1.25(3H, t), 2.33~2.38(2H), 2.57~2.62 (2H), 3.85(3H, s), 4.13(2H, q), 4.57(2H, s), 6.97~7.28(4H) | 291 (CI) |
| 94 | 3-OMe | Et | 1.25(3H, t), 2.39~2.44(2H), 2.58~2.63 | 291 |

TABLE 13-continued

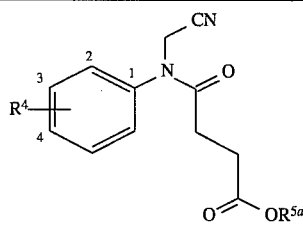

| Ex. No. | R⁴ | R⁵ᵃ | NMR (CDCl₃) δ in ppm scale | MS (m/z) |
|---|---|---|---|---|
|  |  |  | (2H), 3.84(3H, s), 4.12(2H, q), 4.58(2H, s), 6.89–7.43(4H) | (CI) |
| 95 | 3-Et | Et | 1.23–1.30(6H), 2.35–2.40(2H), 2.58–2.63(2H), 2.71(2H, q), 4.13(2H, q), 4.58(2H, s), 7.14–7.43(4H) | 289 (CI) |
| 96 | 2-Me | Et | 1.24(3H, t), 2.15–2.78(4H), 2.32(3H, s), 4.12(2H, q), 4.26(1H, d), 4.83(1H, d), 7.27–7.38(4H) | 275 (CI) |
| 97 | H | Me | 2.34–2.39(2H), 2.58–2.63(2H), 3.65(3H, s), 4.58–4.59(2H), 7.29–7.51(5H) | 247 (CI) |
| 98 | 3-Me | Et | 1.25(3H, t), 2.35–2.41(2H), 2.41(3H, s), 2.58–2.63(2H), 4.13(2H, q), 4.57(2H, s), 7.12–7.40(4H) | 275 (CI) |
| 99 | 2-SCH₃ | Et | 1.25(3H, t), 2.02–2.80(4H), 2.48(3H, s), 4.00(1H, d), 4.12(2H, q), 5.13(1H, d), 7.23–7.48(4H) | 306 (EI) |
| 100 | H | Et | 1.25(3H, t), 2.34–2.39(2H), 2.59–2.63 (2H), 4.12(2H, q), 4.60(2H, s), 7.34–7.54(5H) | 261 (CI) |

The formulation examples of the pharmaceutical composition containing the benzothiazole compound of the formula (I) or a pharmaceutically acceptable salt thereof as an active ingredient, are given in the following.

| Formulation Example 1 | |
|---|---|
| Compound of Example 65 | 20 g |
| Lactose | 315 g |
| Corn starch | 125 g |
| Crystalline cellulose | 25 g |

The above ingredients were homogeneously mixed and added with an aqueous solution (200 ml) of 7.5% hydroxypropylcellulose. The mixture was prepared into granules by an extrusion granulator with the use of a 0.5 mm diameter screen. The granules were immediately rounded and dried. The dry granules were coated with a film coating solution (1.9 kg) of the following composition by a fluid-type granulator to give enteric coated granules.

| Coating solution: | |
|---|---|
| Hydroxypropylmethylcellulose phthalate | 5.0 (w/w) % |
| Stearic acid | 0.25 (w/w) % |
| Methylene chloride | 50.0 (w/w) % |
| Ethanol | 44.75 (w/w) % |

| Formulation Example 2 | |
|---|---|
| Compound of Example 47 | 20 g |
| Lactose | 100 g |
| Corn starch | 36 g |
| Crystalline cellulose | 30 g |
| Calcium carboxymethylcellulose | 10 g |
| Magnesium stearate | 4 g |

The above ingredients were homogeneously mixed and prepared into tablets each weighing 200 mg by a single punch tableting machine with the use of a 7.5 mm diameter punch. Then, the film coating solution of the following composition was spray-coated at 10 mg per tablet to give enteric coated tablets.

| Coating solution: | |
|---|---|
| Hydroxypropylmethylcellulose phthalate | 8.0 (w/w) % |
| Glycerol fatty acid ester | 0.4 (w/w) % |
| Methylene chloride | 50.0 (w/w) % |
| White beewax | 0.1 (w/w) % |
| Isopropanol | 41.5 (w/w) % |

| Formulation Example 3 | |
|---|---|
| Compound of Example 67 | 200 g |
| Polysorbate 80 | 20 g |
| PANASETO ® 810 | 1780 g |

The above ingredients were mixed and completely dissolved. With the use of a film solution for soft capsules composed of gelatin (100 parts), con. glycerine (30 parts), ethyl p-hydroxybenzoate (0.4 part) and propyl p-hydroxybenzoate (0.2 part), soft capsules containing 200 mg of a drug solution per capsule were prepared by a rotary method.

| Formulation Example 4 | |
|---|---|
| Compound of Example 52 | 100 mg |
| Sodium acetate | 2 mg |
| Acetic acid (for adjusting to pH 5.8) | suitable amount |
| Distilled water | residual amount |
|  | Total 10 ml/vial |

An injection having the above formulation was prepared by a conventional method.

| Formulation Example 5 | |
| --- | --- |
| Compound of Example 65 | 0.05 g |
| Polysorbate 80 | 0.2 g |
| Sodium dihydrogenphosphate 2 hydrate | 0.2 g |
| Disodium hydrogenphosphate 12 hydrate | 0.5 g |
| Sodium chloride | 0.75 g |
| Methyl p-hydroxybenzoate | 0.026 g |
| Propyl p-hydroxybenzoate | 0.014 g |
| Sterile purified water | suitable amount |
| | Total 100 ml |

An eye drop having the above formulation was prepared by a conventional method.

Industrial Utilization

The novel compound, benzothiazole compound of the formula (I), and a pharmaceutically acceptable salt thereof of the present invention have an aldose reductase inhibitory activity in mammals inclusive of human and have superior safety. Accordingly, they are useful as pharmaceutical compositions for the treatment of the complications of diabetes, such as faulty union of corneal injury, cataract, neurosis, retinopathy and nephropathy, particularly cataract and neurosis.

The novel compounds of the formula (II) and the formula (IV), inclusive of their salts, can be suitably used as intermediates for the production of the benzothiazole derivatives and pharmaceutically acceptable salts thereof of the present invention.

According to the production method of the present invention, the compound of the formula (I), novel compounds of the formula (II) and the formula (IV) and salts thereof, which are useful as described above, can be efficiently produced.

What is claimed is:

1. A benzothiazole compound of the following formula (I)

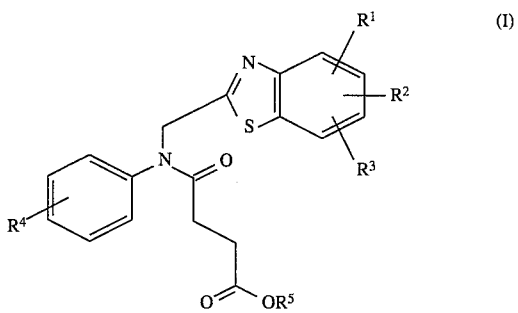

wherein $R^1$ is a halogen atom, $R^2$ and $R^3$ are the same or different and each is a hydrogen atom or a halogen atom, $R^4$ is a hydrogen atom, a halogen atom, a lower alkyl, an alkoxy or an alkylthio and $R^5$ is a hydrogen atom or a lower alkyl, or a pharmaceutically acceptable salt thereof.

2. The benzothiazole compound of claim 1, wherein at least one of $R^1$, $R^2$ and $R^3$ is a fluorine atom or a chlorine atom, or a pharmaceutically acceptable salt thereof.

3. The benzothiazole compound of claim 1, wherein two of $R^1$, $R^2$ and $R^3$ are bonded at the 4 and 5 positions, 5 and 7 positions or 6 and 7 positions, or a pharmaceutically acceptable salt thereof.

4. The benzothiazole compound of claim 1, wherein $R^1$, $R^2$ and $R^3$ are bonded at the 4, 5 and 7 positions, or a pharmaceutically acceptable salt thereof.

5. The benzothiazole compound of claim 1, wherein $R^4$ is a hydrogen atom, a fluorine atom, a chlorine atom, a bromine atom, a methyl, an ethyl, an isopropyl, a methoxy or a methylthio, or a pharmaceutically acceptable salt thereof.

6. The benzothiazole compound of claim 1, wherein $R^5$ is a hydrogen atom, a methyl or an ethyl, or a pharmaceutically acceptable salt thereof.

7. The benzothiazole compound of claim 1, which is selected from the group consisting of
N-(4-chlorophenyl)[(4,5,7-trifluorobenzothiazol-2-yl)methyl]succinamic acid,
N-(4-chlorophenyl)[(4,5-dichlorobenzothiazol-2-yl)methyl] succinamic acid,
N-(4-methylphenyl)[(4,5,7-trifluorobenzothiazol-2-yl)methyl]succinamic acid,
N-(2-chlorophenyl)[(4,5,7-trifluorobenzothiazol-2-yl)methyl]succinamic acid,
N-(4-methoxyphenyl)[(4,5,7-trifluorobenzothiazol-2-yl)methyl]succinamic acid,
N-phenyl[(4,5,7-trifluorobenzothiazol-2-yl)methyl]succinamic acid and
N-(2-methylthiophenyl)[(4,5,7-trifluorobenzothiazol-2-yl)methyl]succinamic acid, or a pharmaceutically acceptable salt thereof.

8. A pharmaceutical composition comprising the benzothiazole compound of claim 1 or a pharmaceutically acceptable salt thereof with a pharmaceutically acceptable carrier.

9. A pharmaceutical composition for treating complications of diabetes, comprising the benzothiazole compound of claim 1 or a pharmaceutically acceptable salt thereof with a pharmaceutically acceptable carrier.

10. A pharmaceutical composition for aldose reductase inhibition, comprising the benzothiazole compound of claim 1 or a pharmaceutically acceptable salt thereof with a pharmaceutically acceptable carrier.

11. A method for inhibiting aldose reductase, comprising administering an effective amount of the benzothiazole compound of claim 1 or a pharmaceutically acceptable salt thereof.

12. A method for preventing and/or treating complications of diabetes, comprising administering an effective amount of the benzothiazole compound of claim 1 or a pharmaceutically acceptable salt thereof.

* * * * *